US010526567B2

(12) United States Patent
Struillou et al.

(10) Patent No.: US 10,526,567 B2
(45) Date of Patent: Jan. 7, 2020

(54) PROCESS FOR THE PREPARATION OF MICROCAPSULES FREE FROM MELAMINE-FORMALDEHYDE

(71) Applicant: Firmenich SA, Geneva (CH)

(72) Inventors: Arnaud Struillou, Geneva (CH); Nicolas Pichon, Villaz (FR); Claudie Bellouard, Geneva (CH)

(73) Assignee: Firmenich SA, Geneva (CH)

( * ) Notice: Subject to any disclaimer, the term of this patent is extended or adjusted under 35 U.S.C. 154(b) by 0 days.

(21) Appl. No.: 15/545,493

(22) PCT Filed: Jan. 22, 2016

(86) PCT No.: PCT/EP2016/051349
§ 371 (c)(1),
(2) Date: Jul. 21, 2017

(87) PCT Pub. No.: WO2016/116604
PCT Pub. Date: Jul. 28, 2016

(65) Prior Publication Data
US 2018/0187132 A1    Jul. 5, 2018

(30) Foreign Application Priority Data
Jan. 23, 2015 (EP) .................................... 15152351

(51) Int. Cl.
| | | |
|---|---|---|
| *A61K 8/11* | (2006.01) | |
| *B01J 13/18* | (2006.01) | |
| *C11D 3/50* | (2006.01) | |
| *B01J 13/14* | (2006.01) | |
| *A61K 8/87* | (2006.01) | |
| *A61K 8/02* | (2006.01) | |
| *A61Q 19/00* | (2006.01) | |

(52) U.S. Cl.
CPC .............. *C11D 3/505* (2013.01); *A61K 8/022* (2013.01); *A61K 8/11* (2013.01); *A61K 8/87* (2013.01); *A61Q 19/00* (2013.01); *B01J 13/14* (2013.01); *B01J 13/185* (2013.01); *A61K 2800/412* (2013.01); *A61K 2800/413* (2013.01)

(58) Field of Classification Search
CPC . A61K 8/022; A61K 8/11; A61K 8/87; A61K 2800/412; A61K 2800/413; A61Q 19/00; B01J 13/14; B01J 13/185; C11D 3/505
See application file for complete search history.

(56) References Cited

U.S. PATENT DOCUMENTS

| | | | |
|---|---|---|---|
| 4,285,720 A | | 8/1981 | Scher et al. |
| 5,456,854 A | * | 10/1995 | Flower ..................... C11D 1/83 |
| | | | 252/363.5 |
| 2007/0202063 A1 | | 8/2007 | Dihora et al. |
| 2015/0252312 A1 | * | 9/2015 | de Villeneuve .... C11D 17/0039 |
| | | | 510/515 |

FOREIGN PATENT DOCUMENTS

| | | |
|---|---|---|
| EP | 1741775 B1 | 4/2009 |
| GB | 2432843 A | 6/2007 |
| GB | 2432850 A | 6/2007 |
| GB | 2432851 A | 6/2007 |
| GB | 2432852 A | 6/2007 |
| WO | WO1997044125 A1 | 11/1997 |
| WO | WO1998050011 A1 | 11/1998 |
| WO | WO2005054422 A1 | 6/2005 |
| WO | WO2007062733 A1 | 6/2007 |
| WO | WO2007062833 A1 | 6/2007 |
| WO | WO2008016684 A1 | 2/2008 |
| WO | WO2008098387 A1 | 8/2008 |
| WO | WO2011154893 A1 | 12/2011 |
| WO | WO2012007438 A1 | 1/2012 |
| WO | WO2012084904 A1 | 6/2012 |
| WO | WO2013026657 A1 | 2/2013 |
| WO | WO2013092375 A1 | 6/2013 |
| WO | WO2013174615 A2 | 11/2013 |

OTHER PUBLICATIONS

What is Polyurea, Elastomer Specialties, Dec. 2002.*
PDA definition of Polyurea, BASF, 2000.*
International Search Report and Written Opinion, application PCT/EP2016/051349 dated Apr. 22, 2016.
Ken Terao et al., Colloids and Surfaces B: Biointerfaces, vol. 37, Issues 3-4, Sep. 1, 2004, pp. 129-132.

* cited by examiner

*Primary Examiner* — Irina S Zemel
(74) *Attorney, Agent, or Firm* — Armstrong Teasdale LLP

(57) ABSTRACT

The present invention relates to a new process for the preparation of melamine-formaldehyde free microcapsules. Microcapsules obtainable by said process are also an object of the invention. Perfuming compositions and consumer products comprising said capsules, in particular perfumed consumer products in the form of home care or personal care products, are also part of the invention.

20 Claims, 2 Drawing Sheets

PROCESS FOR THE PREPARATION OF MICROCAPSULES FREE FROM MELAMINE-FORMALDEHYDE

This application is a 371 filing of International Patent Application PCT/EP2016/051349 filed 22 Jan. 2016, which claims the benefit of European patent application no 15152351.1 filed 23 Jan. 2015

TECHNICAL FIELD

The present invention relates to a new process for the preparation of melamine-formaldehyde free microcapsules. Microcapsules obtainable by said process are also an object of the invention. Perfuming compositions and consumer products comprising said capsules, in particular perfumed consumer products in the form of home care or personal care products, are also part of the invention.

BACKGROUND OF THE INVENTION

One of the problems faced by the perfumery industry lies in the relatively rapid loss of olfactive benefit provided by odoriferous compounds due to their volatility, particularly that of "top-notes". In order to tailor the release rates of volatiles, delivery systems such as microcapsules containing a perfume, are needed to protect and later release the core payload when triggered. A key requirement from the industry regarding these systems is to survive suspension in challenging bases without physically dissociating or degrading. This is referred to as performance in terms of stability for the delivery system. For instance, fragranced personal and household cleansers containing high levels of aggressive surfactant detergents are very challenging for the stability of microcapsules.

Aminoplast microcapsules formed of a melamine-formaldehyde resin have been largely used to encapsulate hydrophobic actives, thus protecting said actives and providing their controlled release. However, capsules such as aminoplast ones suffer from stability problems when used in consumer products comprising surfactants, such as perfumery consumer products, especially after prolonged storage at elevated temperatures. In such products, even though the capsule wall remains intact, the encapsulated active tends to leak out of the capsule by diffusion through the wall due to the presence of surfactants that are able to solubilise the encapsulated active in the product base. The leakage phenomenon reduces the efficiency of the capsules to protect the active and provide its controlled release.

A variety of strategies have been described to improve the stability of oil core-based microcapsules. Cross-linking of capsule walls, with chemical groups such as polyamines and polyisocyanates, has been described as a way to improve stability of microcapsules. WO2011/154893 discloses for instance a process for the preparation of polyurea microcapsules using a combination of aromatic and aliphatic polyisocyanates in specific relative concentrations. Compared to aminoplast, polyurea-based microcapsules present the additional advantage of being free from melamine-formaldehyde. However, these capsules are not always satisfactory in terms of mechanical properties as that are not friable, which can negatively impact their olfactive performance represented by the odor intensity perceived during handling and after intentional breakage e.g. by rubbing.

There is therefore still a need to provide alternative capsules to those known from the prior art, which would be free from melamine-formaldehyde and at the same time olfactively more performing than existing polyurea-based capsules but also as stable as existing melamine-formaldehyde and/or polyurea-based capsules in challenging media such as surfactant-based consumer products.

On the other hand, some prior arts have been describing polyurea-based microcapsules prepared in absence of added polyamine. In particular, WO97/44125 discloses microcapsules prepared by interfacial polymerization process in which polyurea is formed only from an aromatic diisocyanate described as the essential component to form the capsule wall. In this disclosure, an aromatic polyisocyanate having 3 or more isocyanate groups is optionally present but only used as a cross-linking agent. However, although diisocyanates are known to be very reactive and therefore attractive to form a polymeric wall, there are not always considered as suitable component from a safety standpoint. It has been further taught in *Single-particle light scattering study of polyethyleneglycol-grafted poly(ureaurethane) microcapsule in ethanol*, from Ken Terao et al, in Colloids and Surfaces B: Biointerfaces 37 (2004) 129.132 that capsules based on the use of high levels of triisocyanate to make a capsule wall compared to the quantity of oil to be encapsulated showed poor oil retention upon aging. More particularly, according to this article, even if close to an equiweight of polyisocyanate is used to encapsulate large, high log P molecule (di-2-ethylhexylphtalate) expected to show low propension to leakage through a thick capsule wall, the obtained capsules show poor storage stability when placed in organic solvent, with very high leakage of the (di-2-ethylhexylphtalate) out of the capsule, thus suggesting the polyisocyanate (triisocyanate) used is not suited to yield wall capable of preventing core oil leakage in tough media potentially inducing leakage, be organic solvent or aqueous solutions with high levels of surfactants. Therefore, none of those prior arts is disclosing or suggesting that a performing capsule in terms of perfume retention in challenging medium and good olfactive performance could be obtained based on the use of a polyisocyanate other than a diisocyanate that presents the drawbacks mentioned above.

SUMMARY OF THE INVENTION

It has now been found, that contrary to what could be expected based on prior teachings, performing microcapsules encapsulating perfume oil could be obtained with a wall essentially formed from a polyisocyanate other than a diisocyanate. The process of the invention therefore provides a solution to the above-mentioned problems as it allows preparing capsules in the absence of an additional cross-linker with a membrane consisting of polymerised polyisocyanate essentially formed from a polyisocyanate comprising at least three isocyanate functional groups, preferably aromatic and free from diisocyanate. Unexpectedly, even with very limited amounts of such polyisocyanate used, those capsules demonstrate a high performance in terms of stability and olfactive performance.

In a first aspect, the present invention relates to a process for the preparation of a melamine-formaldehyde free microcapsule comprising the steps of:
1) admixing a perfume or flavour oil with at least one polyisocyanate having at least three isocyanate functional groups, preferably aromatic, to form an oil phase, provided that the oil phase is essentially free from diisocyanate;
2) dissolving an ionic surfactant or ionic colloidal stabilizer in water to form a water phase;

3) adding the oil phase to the water phase to form an oil-in-water dispersion, wherein the mean droplet size is comprised between 1 and 500 µm, preferably between 5 and 50 microns;
4) performing a curing step to form a microcapsule slurry; said process being characterized in that the at least one polyisocyanate is present in an amount comprised between 1 and 15% of the oil phase, the water phase is essentially free from melamine-formaldehyde and no amine or polyamine is added at any stage of the process.

In a second aspect, the invention relates to a melamine-formaldehyde free microcapsule obtainable by a process as defined above.

In a third aspect, the invention concerns a perfuming composition comprising
(i) perfume microcapsules as defined above;
(ii) at least one ingredient selected from the group consisting of a perfumery carrier and a perfumery co-ingredient; and
(iii) optionally at least one perfumery adjuvant, In a fourth and fifth aspects, the invention relates to a surfactant-based consumer perfumed product in liquid or powder form, containing microcapsules or a perfuming composition as previously defined.

DETAILED DESCRIPTION OF THE INVENTION

Figure 1:
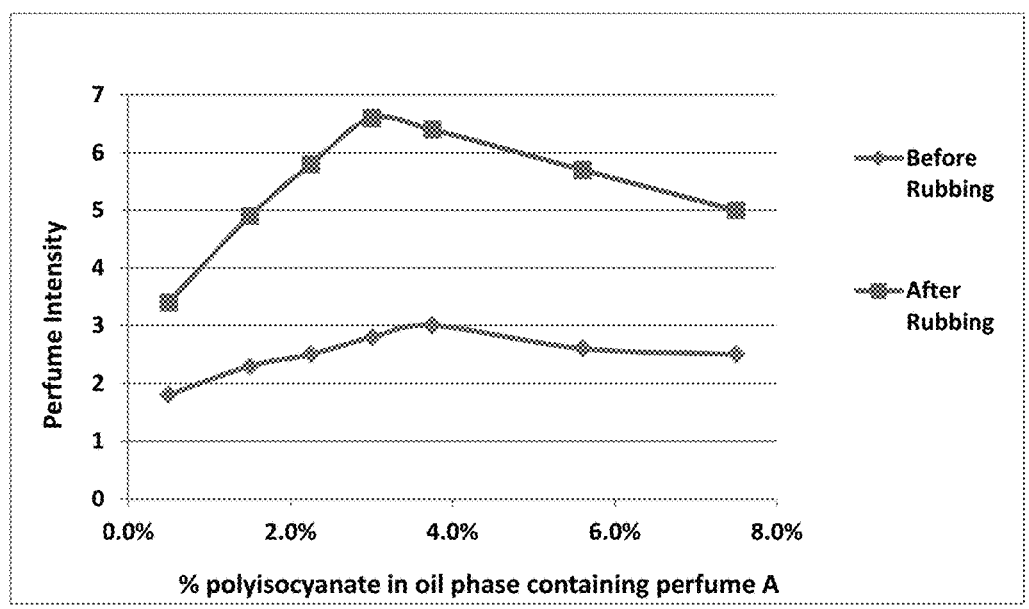
FIG. 1: illustrates the olfactive performance—perfume intensity—of capsules according to the invention as a function of the percentage of polyisocyanate in the oil phase containing perfume A.

Unless stated otherwise, percentages (%) are meant to designate a percentage by weight of a composition.

By "essentially free from melamine-formaldehyde" it is meant that the water phase does not contain an amount of melamine-formaldehyde susceptible of further reacting with the polyisocyanate in a way that would substantially modify the nature of the capsule wall.

By "perfume or flavour oil", it is meant a single perfuming or flavouring compound or a mixture of several perfuming or flavouring compounds.

For the sake of clarity, by the expression "dispersion" in the present invention it is meant a system in which particles are dispersed in a continuous phase of a different composition and it specifically includes a suspension or an emulsion.

In the context of the invention, additional cross-linker or additional cross-linking agent is meant to designate a spacer capable of linking polymeric chains among each other.

It has been found that melamine-formaldehyde free microcapsules with a good performance namely a right balance between stability in a surfactant-based product and odor perception, could be obtained without adding an additional cross-linker, namely a (poly)amine to a process that is based on interfacial polymerisation of a particular polyisocyanate used in limited amounts. This is very surprising in view of the fact that the only processes describing polyurea-based capsules without the addition of a polyamine so far were either using a diisocyanate as an essential ingredient due to its reactivity, or were teaching away from using triisocyanate as the obtained capsules were then described as having a low performance in particular high oil leakage upon storage.

The present invention therefore relates in a first aspect to a process for the preparation of a melamine-formaldehyde free microcapsule comprising the steps of:
1) admixing a perfume or flavour oil with at least one polyisocyanate having at least three isocyanate functional groups—preferably aromatic—to form an oil phase, provided that the oil phase is essentially free from diisocyanate;
2) dissolving an ionic surfactant or ionic colloidal stabilizer in water to form a water phase;
3) adding the oil phase to the water phase to form an oil-in-water dispersion, wherein the mean droplet size is comprised between 1 and 500 µm, preferably between 5 and 50 microns;
4) performing a curing step to form a microcapsule slurry;
5) optionally drying the final dispersion to obtain at least one dried core-shell microcapsule;
said process being characterized in that the at least one polyisocyanate is present in an amount comprised between 1 and 15% of the oil phase, the water phase is essentially free from melamine-formaldehyde and no amine or polyamine is added at any stage of the process.

It has been thus found that in the absence of a diisocyanate, a polyisocyanate comprising at least three isocyanate functional groups—preferably aromatics—even present in limited amount in the oil phase was capable of polymerisation with sufficient efficiency to provide a capsule wall with good properties.

In one step of the process a perfume or flavour oil is therefore added with at least one polyisocyanate—preferably aromatic—having at least three isocyanate functional groups to form an oil phase, provided that the oil phase is essentially free from diisocyanate.

By "perfume oil" (or also "perfume") what is meant here is an ingredient or composition that is a liquid at about 20° C. According to any one of the above embodiments said perfume oil in which the polyisocyanate is dissolved in step 1) can be a perfuming ingredient alone or a mixture of ingredients in the form of a perfuming composition. As a "perfuming ingredient" it is meant here a compound, which is used in perfuming preparation or composition to impart, improve, modify or modulate a hedonic effect. In other words such an ingredient, to be considered as being a perfuming one, must be recognized by a person skilled in the art as being able to at least, as primary purpose, impart, enhance or modulate in a positive or pleasant way the odor of a composition, and not just as having an odor. Perfuming ingredients can also be used for additional benefits than primary one. For example, perfuming ingredients with additional benefits such as malodor counteracting properties are also encompassed by the definition of "perfuming ingredients".

The nature and type of the perfuming ingredients present in the oil phase do not warrant a more detailed description here, which in any case would not be exhaustive, the skilled person being able to select them on the basis of its general knowledge and according to intended use or application and the desired organoleptic effect. In general terms, these perfuming ingredients belong to chemical classes as varied as alcohols, aldehydes, ketones, esters, ethers, acetates, nitriles, terpenoids, nitrogenous or sulphurous heterocyclic compounds and essential oils, and said perfuming co-ingredients can be of natural or synthetic origin. Many of these co-ingredients are in any case listed in reference texts such as the book by S. Arctander, Perfume and Flavor Chemicals, 1969, Montclair, N.J., USA, or its more recent versions, or in other works of a similar nature, as well as in the abundant patent literature in the field of perfumery. It is also understood that said ingredients may also be compounds known to release in a controlled manner various types of perfuming compounds.

The perfuming ingredients may be dissolved in a solvent of current use in the perfume industry. The solvent is preferably not an alcohol. Examples of such solvents are diethyl phthalate, isopropyl myristate, Abalyn® (rosin resins, available from Eastman), benzyl benzoate, ethyl citrate, limonene or other terpenes, or isoparaffins. Preferably, the solvent is very hydrophobic and highly sterically hindered, like for example Abalyn® or benzyl benzoate. Preferably the perfume comprises less than 30% of solvent. More preferably the perfume comprises less than 20% and even more preferably less than 10% of solvent, all these percentages being defined by weight relative to the total weight of the perfume. Most preferably, the perfume is essentially free of solvent.

According to any one of the invention's embodiment, the perfume oil represents between about 10% and 60% w/w, or even between 20% and 45% w/w, by weight, relative to the total weight of the dispersion as obtained after step 3).

By "flavour ingredient or composition" it is meant here a flavouring ingredient or a mixture of flavouring ingredients, solvent or adjuvants of current use for the preparation of a flavouring formulation, i.e. a particular mixture of ingredients which is intended to be added to an edible composition or chewable product to impart, improve, modify or modulate (e.g. in the case of trigeminal actives) its organoleptic properties, in particular its flavour and/or taste. Flavoring ingredients are well known to a skilled person in the art and their nature does not warrant a detailed description here, which in any case would not be exhaustive, the skilled flavorist being able to select them on the basis of his general knowledge and according to the intended use or application and the organoleptic effect it is desired to achieve. Many of these flavouring ingredients are listed in reference texts such as in the book by S. Arctander, Perfume and Flavor Chemicals, 1969, Montclair, N.J., USA, or its more recent versions, or in other works of similar nature such as Fenaroli's Handbook of Flavor Ingredients, 1975, CRC Press or Synthetic Food Adjuncts, 1947, by M. B. Jacobs, can Nostrand Co., Inc. Solvents and adjuvants or current use for the preparation of a flavouring formulation are also well known in the art.

Alternative hydrophobic ingredients which could benefit from being encapsulated could be used either instead of a perfume or flavour, or in combination with a perfume or flavour. Non-limiting examples of such ingredients include a cosmetic, skin caring, malodour counteracting, bactericide, fungicide, pharmaceutical or agrochemical ingredient, a sanitizing agent, an insect repellent or attractant.

Suitable polyisocyanates used according to the invention include aromatic polyisocyanate, aliphatic polyisocyanate and mixtures thereof. Said polyisocyanate comprises at least 3 but may comprise up to 6, or even only 4, isocyanate functional groups. According to a particular embodiment, a triisocyanate (3 isocyanate functional group) is used.

According to one embodiment, said polyisocyanate is an aromatic polyisocyanate. The term "aromatic polyisocyanate" is meant here as encompassing any polyisocyanate comprising an aromatic moiety. Preferably, it comprises a phenyl, a toluyl, a xylyl, a naphthyl or a diphenyl moiety, more preferably a toluyl or a xylyl moiety. Preferred aromatic polyisocyanates are biurets, polyisocyanurates and trimethylol propane adducts of diisocyanates, more preferably comprising one of the above-cited specific aromatic moieties. More preferably, the aromatic polyisocyanate is a polyisocyanurate of toluene diisocyanate (commercially available from Bayer under the tradename Desmodur® RC), a trimethylol propane-adduct of toluene diisocyanate (commercially available from Bayer under the tradename Desmodur® L75), a trimethylol propane-adduct of xylylene diisocyanate (commercially available from Mitsui Chemicals under the tradename Takenate® D-110N). In a most preferred embodiment, the aromatic polyisocyanate is a trimethylol propane-adduct of xylylene diisocyanate.

According to another embodiment, said polyisocyanate is an aliphatic polyisocyanate. The term "aliphatic polyisocyanate" is defined as a polyisocyanate which does not comprise any aromatic moiety. Preferred aliphatic polyisocyanates are a trimer of hexamethylene diisocyanate, a trimer of isophorone diisocyanate, a trimethylol propane-adduct of hexamethylene diisocyanate (available from Mitsui Chemicals) or a biuret of hexamethylene diisocyanate (commercially available from Bayer under the tradename Desmodur® N 100), among which a biuret of hexamethylene diisocyanate is even more preferred.

According to another embodiment, said at least one polyisocyanate is in the form of a mixture of at least one aliphatic polyisocyanate and of at least one aromatic polyisocyanate, both comprising at least two or three isocyanate functional groups, such as a mixture of a biuret of hexamethylene diisocyanate with a trimethylol propane-adduct of xylylene diisocyanate, a mixture of a biuret of hexamethylene diisocyanate with a polyisocyanurate of toluene diisocyanate and a mixture of a biuret of hexamethylene diisocyanate with a trimethylol propane-adduct of toluene diisocyanate. Most preferably, it is a mixture of a biuret of hexamethylene diisocyanate with a trimethylol propane-adduct of xylylene diisocyanate. Preferably, when used as a mixture the molar ratio between the aliphatic polyisocyanate and the aromatic polyisocyanate is ranging from 80:20 to 10:90.

The at least one polyisocyanate used in the process of the invention is present in amounts representing from 1 to 15 wt %, preferably from 2 to 8 wt % and more preferably from 2 to 6 wt % of the oil phase.

According to a particular embodiment, the oil phase essentially consists of the polyisocyanate with at least 3 isocyanate functional groups, and the perfume or flavor oil.

In another step, an ionic surfactant or a colloidal stabilizer ionic at pH>5 is separately solubilized in water to form a water phase. Suitable ionic surfactants include but are not limited to anionic surfactant (such as sodium dodecyl sulphate). Suitable colloidal stabilizers ionic at pH>5 include but are not limited to those selected from the group consisting of co-polymers of acrylamide and acrylic acid (such as Alcapsol® 144 from Ciba), e.g. acid/acrylamide copolymers produced from monomer mixture of acrylic acid and acrylamide wherein the acrylic acid content is in the range of from 30 to 70%, acrylic co-polymers bearing a sulfonate group (such as sodium polystyrene sulfonate), and co-polymers of vinyl ethers and maleic anhydride (once hydrolysed). According to any one of the above embodiments of the present invention, said stabilizer is an ionic surfactant, such as a co-polymers of acrylamide and acrylic acid.

According to any one of the above embodiments of the present invention, the dispersion comprises between about 0.1% and 5% w/w of at least a stabilizer, percentage being expressed on a w/w basis relative to the total weight of the dispersion as obtained after step 3). In still another aspect of the invention, the dispersion comprises between about 0.1% and 2% w/w of at least a stabilizer. In still another aspect of the invention, the dispersion comprises between about 0.1% and 1% w/w of at least a stabilizer.

In the next step of the process of the invention, the oil phase is then added to the water phase to form a dispersion wherein the mean droplet size is comprised between 1 and 500 μm, preferably between 5 and 50 microns. This is followed by a curing step 4) which allows to end up with microcapsules in the form of a slurry or liquid dispersion. According to a preferred embodiment, said step is performed at a temperature comprised between 50 and 130° C., possibly under pressure, for 15 minutes to 8 hours. More preferably it is performed at between 50 and 90° C. for between 30 minutes and 4 hours. Most preferably it is performed between 75 and 90° C. for between 1 and 4 hours.

According to a particular embodiment of the invention, at the end of step 4) one may also add to the invention's slurry a polymer selected from the group consisting of a non-ionic polysaccharide, a cationic polymer and mixtures thereof to form an outer coating to the microcapsule.

Non-ionic polysaccharide polymers are well known to a person skilled in the art and are described for instance in WO2012/007438 page 29, lines 1 to 25 and in WO2013/026657 page 2, lines 12 to 19 and page 4, lines 3 to 12. Preferred non-ionic polysaccharides are selected from the group consisting of locust bean gum, xyloglucan, guar gum, hydroxypropyl guar, hydroxypropyl cellulose and hydroxypropyl methyl cellulose.

Cationic polymers are also well known to a person skilled in the art, e.g. are described in WO2008/098387 page 5, lines 10 to 30. Preferred cationic polymers have cationic charge densities of at least 0.5 meq/g, more preferably at least about 1.5 meq/g, but also preferably less than about 7 meq/g, more preferably less than about 6.2 meq/g. The cationic charge density of the cationic polymers may be determined by the Kjeldahl method as described in the US Pharmacopoeia under chemical tests for Nitrogen determination. The preferred cationic polymers are chosen from those that contain units comprising primary, secondary, tertiary and/or quaternary amine groups that can either form part of the main polymer chain or can be borne by a side substituent directly connected thereto. The weight average (Mw) molecular weight of the cationic polymer is preferably between 10,000 and 2M Dalton, more preferably between 50,000 and 1.5M Dalton. As specific examples, one may cite Salcare® SC60 (cationic copolymer of acrylamidopropyltrimonium chloride and acrylamide, origin: BASF) or Luviquat®, such as the PQ 11N, FC 550 or Supreme (polyquaternium-11 to 68 or quaternized copolymers of vinylpyrrolidone origin: BASF), or also the Jaguar® (C135 or C17, origin Rhodia).

According to any one of the above embodiments of the invention, there is added an amount of polymer described above comprised between about 0% and 5% w/w, or even between about 0.1% and 2% w/w, percentage being expressed on a w/w basis relative to the total weight of the slurry as obtained after step 4). It is clearly understood by a person skilled in the art that only part of said added polymers will be incorporated into/deposited on the microcapsule shell.

Alternatively, in the optional step 5), the slurry obtained by the process described above can be submitted to a drying, like spray-drying, to provide the microcapsules as such, i.e. in a powdery form. It is understood that any standard method known by a person skilled in the art to perform such drying is also applicable. In particular the slurry may be spray-dried preferably in the presence of a polymeric carrier material such as polyvinyl acetate, polyvinyl alcohol, dextrins, natural or modified starch, vegetable gums, pectins, xanthans, alginates, carragenans or cellulose derivatives to provide microcapsules in a powder form.

Capsules obtainable by the process above-described are also an object of the invention. Despite the nature of the polyisocyanate forming the membrane and despite the fact that the membrane is relatively thin in view of the limited amount of polyisocyanate used during the process, the capsules of the invention show very good performance in terms of stability in challenging medium and good mechanical properties which translate into good odor performance. In this regard it has to be mentioned that although ideal situation would be one where microcapsules show best stability, i.e. lowest perfume leakage in application combined with best odor performance, i.e. perfume intensity in application both before rubbing and after rubbing, different scenarios can be very interesting depending on the application and slightly less stable capsules with higher odor performance can be very useful and so could more stable capsules with slightly lower odor performance. The capsules of the invention have a profile perfume leakage/odor performance that varies depending on the proportion of polyisocyanate and the nature of the perfume oil. A skilled person in the art is capable of choosing the best balance depending on the needs in application. The capsules according to the invention present the additional advantage of being free from melamine-formaldehyde.

Another object of the present invention is a perfuming composition comprising:
(i) Perfume microcapsules as defined above;
(ii) At least one ingredient selected from the group consisting of a perfumery carrier, a perfumery co-ingredient and mixtures thereof;
(iii) Optionally at least one perfumery adjuvant.

As liquid perfumery carrier one may cite, as non-limiting examples, an emulsifying system, i.e. a solvent and a surfactant system, or a solvent commonly used in perfumery. A detailed description of the nature and type of solvents commonly used in perfumery cannot be exhaustive. However, one can cite as non-limiting examples solvents such as dipropyleneglycol, diethyl phthalate, isopropyl myristate, benzyl benzoate, 2-(2-ethoxyethoxy)-1-ethanol or ethyl citrate, which are the most commonly used. For the compositions which comprise both a perfumery carrier and a perfumery co-ingredient, other suitable perfumery carriers than those previously specified, can be also ethanol, water/ethanol mixtures, limonene or other terpenes, isoparaffins such as those known under the trademark Isopar® (origin: Exxon Chemical) or glycol ethers and glycol ether esters such as those known under the trademark Dowanol® (origin: Dow Chemical Company). By "perfumery co-ingredient" it is meant here a compound, which is used in a perfuming preparation or a composition to impart a hedonic effect and which is not a microcapsule as defined above. In other words such a co-ingredient, to be considered as being a perfuming one, must be recognized by a person skilled in the art as being able to impart or modify in a positive or pleasant way the odor of a composition, and not just as having an odor.

The nature and type of the perfuming co-ingredients present in the perfuming composition do not warrant a more detailed description here, which in any case would not be exhaustive, the skilled person being able to select them on the basis of his general knowledge and according to the intended use or application and the desired organoleptic effect. In general terms, these perfuming co-ingredients belong to chemical classes as varied as alcohols, lactones, aldehydes, ketones, esters, ethers, acetates, nitriles, terpenoids, nitrogenous or sulphurous heterocyclic compounds and essential oils, and said perfuming co-ingredients can be of natural or synthetic origin. Many of these co-ingredients are in any case listed in reference texts such as the book by S. Arctander, Perfume and Flavor Chemicals, 1969, Montclair, N.J., USA, or its more recent versions, or in other works of a similar nature, as well as in the abundant patent literature in the field of perfumery. It is also understood that said co-ingredients may also be compounds known to release in a controlled manner various types of perfuming compounds.

By "perfumery adjuvant" we mean here an ingredient capable of imparting additional added benefit such as a color, a particular light resistance, chemical stability, etc. A detailed description of the nature and type of adjuvant commonly used in perfuming bases cannot be exhaustive, but it has to be mentioned that said ingredients are well known to a person skilled in the art.

Preferably, the perfuming composition according to the invention comprises between 0.05 to 30%, preferably between 0.1 and 30% by weight of microcapsules as defined above.

The invention's microcapsules can advantageously be used in all the fields of modern perfumery, i.e. fine or functional perfumery. Consequently, another object of the present invention is represented by a perfuming consumer product comprising as a perfuming ingredient, the microcapsules defined above or a perfuming composition as defined above.

The invention's microcapsules can therefore be added as such or as part of an invention's perfuming composition in a perfuming consumer product.

For the sake of clarity, it has to be mentioned that, by "perfuming consumer product" it is meant a consumer product which is expected to deliver at least a pleasant perfuming effect to the surface to which it is applied (e.g. skin, hair, textile, or home surface). In other words, a perfuming consumer product according to the invention is a perfumed consumer product which comprises a functional formulation, as well as optionally additional benefit agents, corresponding to the desired consumer product, e.g. a detergent or an air freshener, and an olfactive effective amount of at least one invention's compound.

The nature and type of the constituents of the perfumery consumer product do not warrant a more detailed description here, which in any case would not be exhaustive, the skilled person being able to select them on the basis of his general knowledge and according to the nature and the desired effect of said product. Formulations of consumer products in which the microcapsules of the invention can be incorporated can be found in the abundant literature relative to such products. These formulations do not warrant a detailed description here which would in any case not be exhaustive.

The person skilled in the art of formulating such consumer products is perfectly able to select the suitable components on the basis of his general knowledge and of the available literature.

In particular, examples of such formulations can be found in the patents and patent applications relative to such products, for example in WO2008/016684, US2007/0202063, WO2007/062833, WO2007/062733, WO2005/054422, EP1741775, GB2432843, GB2432850, GB2432851, GB2432852, WO 9850011, WO2013174615 or WO2012084904.

Non-limiting examples of suitable perfumery consumer product can be a perfume, such as a fine perfume, a cologne or an after-shave lotion; a fabric care product, such as a liquid or solid detergent, tablets and pods, a fabric softener, a dryer sheet, a fabric refresher, an ironing water, or a bleach; a body-care product, such as a hair care product (e.g. a shampoo, hair conditioner, a colouring preparation or a hair spray), a cosmetic preparation (e.g. a vanishing cream, body lotion or a deodorant or antiperspirant), or a skin-care product (e.g. a perfumed soap, shower or bath mousse, body wash, oil or gel, bath salts, or a hygiene product); an air care product, such as an air freshener or a "ready to use" powdered air freshener; or a home care product, such all-purpose cleaners, liquid or power or tablet dishwashing products, toilet cleaners or products for cleaning various surfaces, for example sprays & wipes intended for the treatment/refreshment of textiles or hard surfaces (floors, tiles, stone-floors etc.).

Preferably, the consumer product comprises from 0.05 wt %, preferably from 0.1 to 15 wt %, more preferably between 0.2 and 5 wt % of the microcapsules of the present invention, these percentages being defined by weight relative to the total weight of the consumer product. Of course the above concentrations may be adapted according to the olfactive effect desired in each product.

The capsules of the invention have proven to be particularly and advantageously stable in consumer products containing significant amount of surfactant and more particularly they demonstrated an improved stability compared to capsules wherein only one type of particles is used.

The invention will now be further described by way of examples. It will be appreciated that the invention as claimed is not intended to be limited in any way by these examples.

EXAMPLES

Example 1

Preparation of Capsules A to U

Note:

Capsules A to F and I to M and O to U are capsules according to the invention.

Capsules G, H and N are outside the scope of the invention for comparison purposes.

Microcapsules A to U were prepared with the following ingredients:

TABLE 1

Composition of Capsules A to U

| Ingredient | Capsules A to G and I to T Amount [g] | Capsules H Amount [g] | Capsules U Amount [g] |
|---|---|---|---|
| Oil Phase | Variable | 21.57 | Variable |
| Perfume oil (perfume A, perfume B, perfume C or perfume D)[1] | 20.74 | 20.74 | 20.74 |
| Polyisocyanate[2] | variable | 0.83 | 1.04 |
| Water phase | | | |
| acrylamide and acrylic acid copolymer[3] | 4.99 | 4.99 | 4.99 |
| Guanidine carbonate | 0 | 1.13 | 0 |
| Water | 29.35 | 29.35 | 29.35 |
| Sodium hydroxyde | 0.3 | 0.3 | 0.3 |
| Acetic acid | 0.2 | 0.2 | 0.2 |
| Salcare ® SC60[4] | 11.34 | 11.34 | 21.80 |

[1] see Table 3, Table 4, Table 5 or Table 6
[2] Takenate ® D-110N (trimethylol propane adduct of xylylene diisocyanate); origin and trademark from Mitsui Chemicals, 75% polyisocyanate/25% ethyl acetate
[3] Alcapsol ™; origin and trademark from Ciba, 20% solution in water
[4] Salcare ® SC60; origin and trademark from Ciba, (acrylamidopropyltrimonium chloride/acrylamide copolymer), 3% solution in water Process for Making Microcapsules A to U:

The oil phase was prepared by admixing a variable amount of polyisocyanate (trimethylol propane adduct of xylylene diisocyanate, Takenate® D-110N, origin and trademark from Mitsui Chemicals) in the quantities defined in Table 2 below with 20.74 g of perfume oil A, B, C or D (compositions defined in Tables 3, 4, 5 and 6).

To make the capsules slurry, the acrylamide/acrylic acid copolymer was dissolved in water to form the water phase. Then the perfume/polyisocyanate premix oil phase was added into this solution and the pH was regulated to 5 with acetic acid. The temperature was raised to 90° C. for 2 hours to allow the curing of the capsules. At this point, capsules were formed, cross-linked and stable. A 3% Salcare® SC60 solution in water was then added into the mixture at 90° C. and was allowed to react for 1 hour at 90° C. The mixture was left to cool down to room temperature. The final pH was adjusted to 7 with sodium hydroxide.

For capsules H (outside the invention), a polyamine (guanidine carbonate) was added to the water phase before the temperature was raised to 90° C. so that it could react with the polyisocyanate at the interface to form a polyurea. Capsules H are outside the scope of the invention.

The variable amounts of the polyisocyanate used to make the capsule wall of Capsules A to U are summarized in the table 2 below:

TABLE 2

Variable weight of Takenate D-110N mixed with 20.74 g of perfume oil A, B, C or D to prepare capsules A to U

| | A | B | C | D | E | F | G | H |
|---|---|---|---|---|---|---|---|---|
| Weight of Takenate ® D-110N used (g) | 2.07 | 1.56 | 1.04 | 0.83 | 0.62 | 0.41 | 0.14 | 1.04 |
| % of commercial Takenate ® D-110N in oil phase | 10 | 7.5 | 5 | 4 | 3 | 2 | 0.66 | 5 |
| % of pure polyisocyanate in oil phase | 7.5 | 5.6 | 3.75 | 3 | 2.25 | 1.5 | 0.5 | 3.75 |

| | I | J | K | L | M | N |
|---|---|---|---|---|---|---|
| Weight of Takenate ® D-110N used (g) | 2.07 | 1.56 | 1.04 | 0.62 | 0.41 | 0.14 |
| % of commercial Takenate ® D-110N in oil phase | 10 | 7.5 | 5 | 3 | 2 | 0.66 |
| % of pure polyisocyanate in oil phase | 7.5 | 5.6 | 3.75 | 2.25 | 1.5 | 0.5 |

| | O | P | Q | R | S |
|---|---|---|---|---|---|
| Weight of Takenate ® D-110N used (g) | 2.07 | 1.56 | 1.04 | 0.62 | 0.41 |
| % of commercial Takenate ® D-110N in oil phase | 10 | 7.5 | 5 | 3 | 2 |
| % of pure polyisocyanate in oil phase | 7.5 | 5.6 | 3.75 | 2.25 | 1.5 |

| | T | U |
|---|---|---|
| Weight of Takenate ® D-110N used (g) | 1.04 | 1.04 |
| % of commercial Takenate ® D-110N in oil phase | 5 | 5 |

TABLE 2-continued

Variable weight of Takenate D-110N mixed with 20.74 g of perfume oil A, B, C or D to prepare capsules A to U

| | | |
|---|---|---|
| % of pure polyisocyanate in oil phase | 3.75 | 2.25 | pure polyisocyanate = 75% of quantity of Takenate ® D-110N used

After encapsulation and use of the Takenate® D-110N to produce the capsule wall, the residual level of unreacted polyisocyanate in the perfume oil was very low and therefore the internal core of the capsule was essentially made of the perfume oil.

TABLE 3

Composition of Perfume A

| Raw mat | % in formula |
|---|---|
| Ethyl-2-methyl butyrate | 1.50% |
| Amyl Acetate | 1.00% |
| Ethyl 2-methyl-pentanoate | 3.80% |
| Ethyl Hexanoate | 0.35% |
| (Z)-3-hexen-1-ol acetate | 2.00% |
| Hexyl Acetate | 11.50% |
| Methylparacresol | 0.10% |
| Eucalyptol | 0.15% |
| Allyl Hexanoate | 4.00% |
| 2,4-Dimethyl-3-cyclohexene-1-carbaldehyde[1] | 2.00% |
| Rose oxide | 0.25% |
| Fructone ®[2] | 1.20% |
| Benzyl Acetate | 0.75% |
| Allyl Heptanoate | 1.60% |
| Anisaldehyde | 0.40% |
| Phenylethyl Acetate | 5.60% |
| Undecavertol ®[3] | 0.65% |
| Verdox ™[4] | 25.60% |
| Isoeugenol | 0.10% |
| Citronellyl Acetate | 4.55% |
| Damascone Delta | 0.25% |
| Geranyl Acetate | 3.35% |
| Dicyclopentadiene acetate | 19.70% |
| Yara Yara | 0.20% |
| g-n-decalactone | 1.20% |
| Iso Methylionone alpha | 1.20% |
| Lilial ®[5] | 0.75% |
| 2,2,2-trichloro-1-phenylethyl acetate[6] | 1.10% |
| Undecalactone gamma | 2.50% |
| Methylnaphtyl Ketone | 0.60% |
| Hedione ®[7] | 1.15% |
| (Z)-3-hexen-1-ol salicylate | 0.25% |
| Isocyclemone ® E[8] | 0.10% |
| Hexyl Salicylate | 0.10% |
| Galaxolide ®[9] | 0.45% |
| TOTAL | 100% |

[1]Origin: Firmenich SA, Geneva, Switzerland
[2]2-methyl-1,3-dioxalane-2-acetate d'ethyle, origin and trademark from IFF, USA
[3]4-methyl-3-decen-5-ol; origin and trademark from Givaudan SA, Switzerland
[4]2-tert-butyl-1-cyclohexyl acetate; origin and trademark from IFF, USA
[5]3-(4-tert-butylphenyl)-2-methylpropanal; Origin and trademark from Givaudan SA, Switzerland
[6]Origin: Firmenich SA, Geneva, Switzerland
[7]Methyl dihydrojasmonate; origin and Trademark from Firmenich SA, Geneva, Switzerland
[8]2-acetonaphtone-1,2,3,4,5,6,7,8-octahydrotramethyl; origin and trademark from IFF, USA;
[9]1,3,4,6,7,8-hexahydro-4,6,6,7,8,8-hexamethyl-cyclopenta-g-2-benzopyrane; origin and trademark from IFF, USA

TABLE 4

Composition of perfume B

| Raw mat | % in oil |
|---|---|
| Ethyl 2-methyl-pentanoate | 3.20% |
| Eucalyptol | 7.80% |
| 2,4-Dimethyl-3-cyclohexene-1-carbaldehyde[1] | 0.75% |
| Aldehyde C10 | 0.75% |
| Citronellyl Nitrile | 4.30% |
| Isobornyl acetate | 3.00% |
| Verdox ®[2] | 9.80% |
| Citronellyl Acetate | 1.30% |
| 2-Methylundecanal | 3.00% |
| Diphenyloxide | 0.80% |
| Aldehyde C12 | 1.30% |
| Dicyclopentadiene acetate | 9.85% |
| Ionone beta | 3.30% |
| Undecalactone gamma | 18.75% |
| Hexyl Salicylate | 15.90% |
| Benzyl Salicylate | 16.20% |
| TOTAL | 100% |

[1]Origin: Firmenich SA, Geneva, Switzerland
[2]2-tert-butyl-1-cyclohexyl acetate, origin and trademark from IFF, USA

TABLE 5

Composition of perfume C

| Raw Mat | % in oil |
|---|---|
| Ethyl-2-methyl butyrate | 2.30% |
| Hexyl Acetate | 11.20% |
| Dihydromyrcenol | 11.20% |
| 2,4-Dimethyl-3-cyclohexene-1-carbaldehyde[1] | 3.40% |
| Phenylethyl Acetate | 2.80% |
| Undecavertol ®[2] | 5.60% |
| 2-methylundecanal | 11.20% |
| Delta Damascone | 1.20% |
| Diphenyloxyde | 2.80% |
| Verdyle acetate | 28.00% |
| Lilial ®[3] | 11.20% |
| Amyl Salicylate | 2.30% |
| Hexyl Salicylate | 6.80% |
| Total | 100% |

[1]Origin: Firmenich SA, Geneva, Switzerland
[2]4-methyl-3-decen-5-ol; origin and trademark from Givaudan SA, Switzerland
[3]3-(4-tert-butylphenyl)-2-methylpropanal; origin and trademark from Givaudan SA, Switzerland

TABLE 6

Composition of perfume D

| Raw Mat | % in oil |
|---|---|
| Ethyl 2-methyl-pentanoate[1] | 4.00% |
| 2,4-Dimethyl-3-cyclohexene-1-carbaldehyde[2] | 4.00% |
| Allyl Heptanoate | 6.60% |
| (Z)-3-hexen-1-ol Butyrate | 1.30% |

TABLE 6-continued

Composition of perfume D

| Raw Mat | % in oil |
|---|---|
| Allyl amyl glycolate | 13.10% |
| Delta Damascone | 2.00% |
| Verdyl acetate | 24.30% |
| Methylnaphtylcetone | 1.30% |
| Hedine ®[3)] | 6.60% |
| Iso E Super ®[4)] | 19.70% |
| Ald. Hexylcinnamique | 13.10% |
| Habanolide ®[5)] | 4.00% |
| Total | 100% |

[1)2)]Origin: Firmencih SA, Geneva, Switzerland
[3)]Methyl dihydrojasmonate; origin and trademark from Firmenich SA, Switzerland
[4)]1-(octahydro-2,3,8,8-tetramethyl-2-naphtalenyl)-1-ethanone; origin and trademark from IFF, USA
[5)]Pentadecenolide; origin and trademark from Firmenich SA, Switzerland Example 2

Encapsulation Yield for Capsules Prepared According to Example 1

Efficiency of the encapsulation process was evaluated by determining the amount of perfume oil which has not been encapsulated and by subtraction, the encapsulation yield, namely the proportion of the perfume oil engaged which is encapsulated at the end of the curing step. To this end, the aqueous dispersion of capsules of the invention was quickly washed with a suitable solvent known not to induce leakage of the encapsulated perfume but also suitable to extract all the perfume oil which has not been encapsulated. The percentage of the initial perfume which has not been encapsulated by the end of the curing step (% Not Encapsulated) was determined by GC-MS analysis against calibration curves. The encapsulation yield could then be calculated as being 100% —% Not Encapsulated.

TABLE 7

Encapsulation yield of capsules A to F of the invention and G (not part of the invention) as function of % Takenate ® in the Perfume A oil

| Capsule | % Takenate ® D110N in perfume oil A | Equivalence % polyisocyanate in perfume oil A | Encapsulation yield % |
|---|---|---|---|
| A | 10% | 7.50% | 99.6% |
| B | 7.50% | 5.6% | 99.5% |
| C | 5% | 3.75% | 99.3% |
| D | 4% | 3% | 99.1% |
| E | 3% | 2.25% | 98.9% |
| F | 2% | 1.5% | 92% |
| G | 0.66% | 0.5% | 60% |

The results are showing that good encapsulation can be achieved with capsules according to the invention. Very little polyisocyanate is needed in the perfume oil to obtain very good encapsulation yield. It is already 92% with only 1.5% triisocyanate in the perfume oil A and reaches close to 100% encapsulation yield when more than 2% triisocyanate is used in the perfume oil A. On the other hand, there is a sharp drop in encapsulation efficiency at a triisocyanate concentration in perfume oil A outside of the invention's scope as encapsulation yield is only 60% for capsule G (0.5% of triisocyanate in perfume oil).

TABLE 8

Encapsulation yield of capsules I to M according to the invention and N (not part of the invention) as function of % Takenate ® in the Perfume B oil

| Capsule | % Takenate ® D110N in Perfume oil B | Equivalence % polyisocyanate in perfume oil B | Encapsulation yield % |
|---|---|---|---|
| I | 10% | 7.50% | 99.97% |
| J | 7.5% | 5.6% | 99.97% |
| K | 5% | 3.75% | 99.97% |
| L | 3% | 2.25% | 99.94% |
| M | 2% | 1.5% | 99.9% |
| N | 0.66% | 0.5% | 75% |

As for Perfume A, capsules I to M of the invention were efficiently produced with triisocyanate as sole monomer for the capsule walls (in the absence of polyamine). Again, very little Takenate® D-110N was needed in perfume oil B to get very good encapsulation yield as with 1.5% triisocyanate in perfume oil, more than 99% encapsulation yield was obtained. However, there is a sharp drop in encapsulation efficiency outside the invention as encapsulation yield is only 75% for capsule N.

TABLE 9

Encapsulation yield of capsules O to S according to the invention as function of % Takenate ® in the Perfume C oil

| Capsule | % Takenate ® D110N in Perfume oil C | Equivalence % polyisocyanate in perfume oil C | Encapsulation yield % |
|---|---|---|---|
| O | 10% | 7.50% | 99.97% |
| P | 7.5% | 5.6% | 99.97% |
| Q | 5% | 3.75% | 99.97% |
| R | 3% | 2.25% | 99.94% |
| S | 2% | 1.5% | 99.9% |

As for Perfume A and B, capsules O to S of the invention were efficiently produced with triisocyanate as sole monomer for the capsule walls (in the absence of polyamine). Again, very little Takenate® D-110N was needed in perfume oil C to get very good encapsulation yield as with 1.5% triisocyanate in perfume oil, more than 99% encapsulation yield was obtained.

TABLE 10

Encapsulation yield of capsules T to U according to the invention as function of % Takenate ® in the Perfume D oil

| Capsule | % Takenate ® D110N in Perfume oil D | Equivalence % polyisocyanate in perfume oil D | Encapsulation yield % |
|---|---|---|---|
| T | 5% | 3.75% | 99.97% |
| U | 5% | 3.75% | 99.94% |

As for Perfume A, B and C, capsules T and U of the invention were efficiently produced with triisocyanate as sole monomer (used as 5% in perfume oil) for the capsule walls (in the absence of polyamine).

Example 3

Fabric Softener Containing Capsules

A concentrated un-perfumed fabric softener base was prepared by admixing the ingredients listed in Table 11, in the amounts indicated. The percentages are defined by weight relative to the total weight of the un-perfumed fabric softener base.

TABLE 11

Formulation of the concentrated unperfumed fabric softener base (pH ~2.85)

| Ingredient | % |
|---|---|
| Stepantex VL90 A Diester Quat[1] | 11.00 |
| Proxel ™ GXL[2] | 0.04 |
| CaCl$_2$ (10% aqueous solution) | 0.20 |
| Water | 88.76 |

[1] Ammonium methyl bis[ethyl (sulf)]-2-hydroxyethyl methosulfate; Origin: Stepan
[2] 20% aqueous dipropylene glycol solution of 1,2-benzisothiazolin-3-one; Origin: Avecia Softeners A to N were prepared by adding Capsules A to N at 0.45% by weight, relative to the total weight of the softener into the un-perfumed softener base of Table 11 under gentle shaking.

Example 4

Olfactive Performance of Capsules According to the Invention and Comparison with Capsules not Part of the Invention The olfactive performance of Capsules A to F of the invention and G (outside the invention) (all with encapsulated perfume A) was evaluated in fabric softener of Example 3. Cotton terry towels (20 pieces, 18 cm*18 cm, about 30 g each) were washed with 30 g of un-perfumed detergent (standard powder) in a washing machine (Miele Novotronic W300-33CH) at 40° C. using the short cycle program. The wash was followed by a rinse at 900 rpm with 12.7 g of the Softeners A to G. The terry towels were then line dried for 24 hours before being evaluated.

The intensity of the perception of the perfume on the dry towels treated with Softeners A to G was evaluated by a panel of 20 trained panellists. They were asked to evaluate the towels before rubbing (with very gentle handling— picking them up and bringing them to their nose for smelling) first, then in a second stage, after rubbing the towels in their hands. At both stages, they were asked to rate the intensity of the perfume perception on a scale ranging from 1 to 10, wherein 1 means no odour and 10 means very strong odour. The results are summarized in the following table 12.

TABLE 12

Olfactive performance of capsules A to F of the invention and G (outside the invention) in fabric-softener of Example 3, as a function of % triisocyanate in Perfume oil A

| | % Takenate | Equivalence | Perfume intensity | |
|---|---|---|---|---|
| Capsule | D-110N in perfume oil A | % polyisocyanate in perfume oil A | Before Rubbing | After Rubbing |
| A | 10 | 7.50 | 2.5 | 5 |
| B | 7.50 | 5.6 | 2.6 | 5.7 |
| C | 5 | 3.75 | 3 | 6.4 |
| D | 4 | 3 | 2.8 | 6.6 |
| E | 3 | 2.25 | 2.5 | 5.8 |
| F | 2 | 1.5 | 2.3 | 4.9 |
| G | 0.66 | 0.5 | 1.8 | 3.4 |

Results are represented on FIG. 1.

Olfactively, all capsules A to F made according to the invention, namely using only a triisocyanate as sole monomer for the capsule walls at a concentration of at least 1% in the oil, do exhibit the required profile of some medium impact before rubbing, strongly amplified after rubbing (rubbing effect). Best olfactive performance is achieved when 2% to 6% polyisocyanate is added in the perfume oil.

Capsule G using very low concentration of triisocyanate outside the scope of this invention is olfactively weaker than all capsules A to F of the invention, showing poorer impact both before & after rubbing.

The olfactive performance of Capsules I to M (made according to the invention but this time with encapsulated perfume B) was also evaluated in fabric softener of Example 3, using the same protocol as described above for the olfactive performance of capsules A to G (with encapsulated perfume A). They were compared to the olfactive performance of Capsule N made using concentration of triisocyanate outside the scope of the invention. The results are summarized in the following Table 13.

TABLE 13

Olfactive performance of capsules I to M of the invention and N (outside the invention) in fabric-softener of Example 3, as a function of % triisocyanate in Perfume oil B

| | % Takenate ® | Equivalence | Perfume intensity | |
|---|---|---|---|---|
| Capsule | D-110N in perfume oil B | % polyisocyanate in perfume oil B | Before Rubbing | After Rubbing |
| I | 10% | 7.50% | 2.2 | 3.65 |
| J | 7.50% | 5.6% | 2.2 | 5.25 |
| K | 5% | 3.75% | 2.65 | 6.1 |
| L | 3% | 2.25% | 3.8 | 7.25 |
| M | 2% | 1.5% | 4.55 | 7.1 |
| N | 0.66% | 0.5% | 1.7 | 3.0 |

Figure 2:
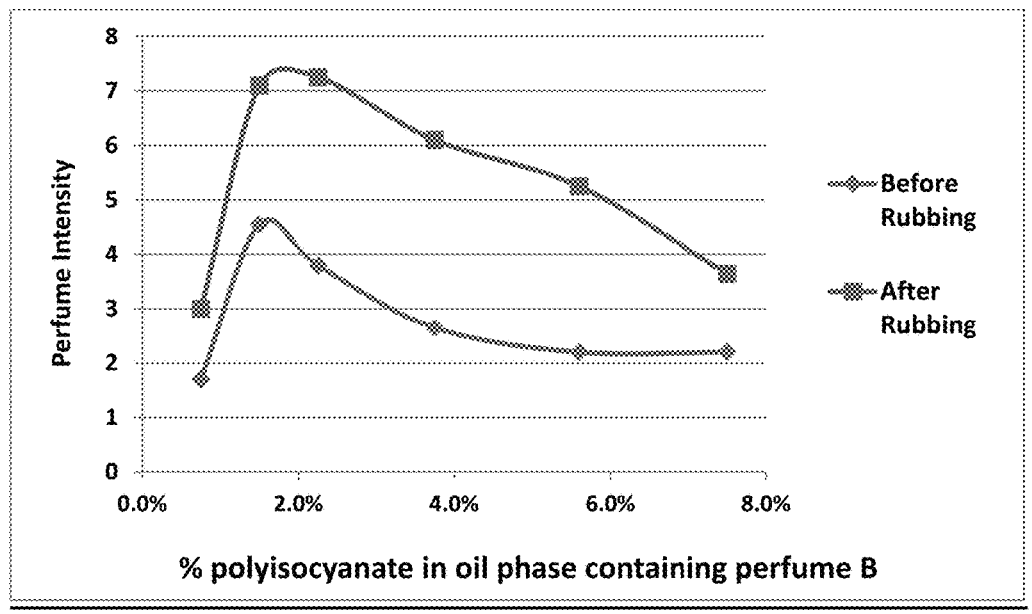
FIG. 2: illustrates the olfactive performance—perfume intensity—of capsules according to the invention as a function of the percentage of polyisocyanate in the oil phase containing perfume B.

Results are represented on FIG. 2.

Again, all capsules I to M made according to the invention with at least 1% triisocyanate as sole monomer for the capsule wall do exhibit the required profile of some medium impact before rubbing, strongly amplified after rubbing (rubbing effect). Best olfactive performance is achieved when 1.5% to 5% polyisocyanate is added in the perfume oil. As for capsule G, capsule N made using concentration of triisocyanate outside the scope of this invention is olfactively weaker than all capsules I to M of the invention, showing significantly poorer impact both before & after rubbing.

Example 5

Storage Stability of Capsules According to the Invention in the Fabric Softener of Example 3

The storage stability of the capsules A to F (made according to the invention) in the fabric-softener of example 3 was evaluated for up to one month at 35° C. or 43° C. Storage stability of capsules G (outside the scope of this invention) was also evaluated. The amount of perfume A having leaked out of the capsules overtime was measured by solvent extraction and GC-MS analysis. The results are summarized in the following table 14.

TABLE 14

Storage stability of capsules A to F of the invention and G (outside the invention) in fabric softener of Example 3: Percentage of perfume leaking overtime upon storage in softener at 35° C. or 43° C.

| Capsule | % Takenate® D-110N in perfume oil A | Equivalence % polyisocyanate in perfume oil A | % perfume leaking out of the capsule upon storage in softener for | | | |
|---|---|---|---|---|---|---|
| | | | 15 days | | 30 days | |
| | | | 35° C. | 43° C. | 35° C. | 43° C. |
| A | 10% | 7.50% | 0.5 | 3 | 1 | 5 |
| B | 7.50% | 5.6% | 1 | 8 | 3 | 12 |
| C | 5% | 3.75% | 3 | 12 | 4 | 18 |
| D | 4% | 3% | 5 | 18 | 7 | 25 |
| E | 3% | 2.25% | 22 | 42 | 28 | 53 |
| F | 2% | 1.5% | 33 | 55 | 40 | 65 |
| G | 0.66% | 0.5% | 55 | 76 | 62 | 85 |

Figure 3:
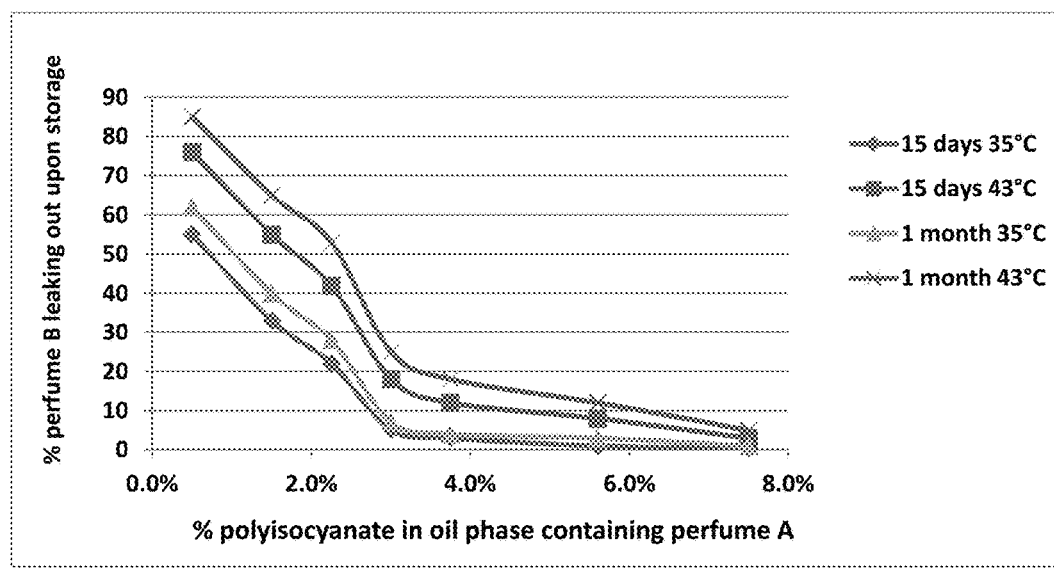
FIG. 3: represents the leakage of encapsulated perfume A upon storage in a fabric softener at 43° C. as a function of the percentage of polyisocyanate in the oil phase.

Results are represented on FIG. 3.

The more polyisocyanate added in the oil, the better the stability (thicker wall), with a sharp gain in stability at the low Takenate® D-110N values and a plateau above 4% Takenate®D-110N in the oil (all capsules are very stable). Capsules A to F made according to the invention show leakage below 40% after 2 weeks storage or 65% after 4 weeks at high temperature, while outside the scope of the invention, the capsule wall leads to very high perfume leakage upon storage (respectively 76% and 85% leakage after 2 & 4 weeks at 43° C. for capsule G outside the scope of this invention).

For this perfume A, optimum between encapsulation efficiency, stability & performance is around 4% to 8% Takenate® D-110N in the oil to be encapsulated which is equivalent to about 3% to 6% pure polyisocyanate added to the perfume oil A to be encapsulated.

The storage stability of the capsules I to M according to the invention was also evaluated in the fabric-softener of Example 3 for up to one month at 35° C. or 43° C. Storage stability of capsules N (outside the scope of this invention) was also evaluated. The amount of perfume B having leaked out of the capsules overtime was measured by solvent extraction and GC-MS analysis. The results are summarized in the following table 15.

TABLE 15

Storage stability of capsules I to M of the invention and N (outside the invention) upon storage in fabric softener of example 3: % perfume leaking overtime upon storage in softener at 43° C.

| Capsule | % Takenate® D-110N in perfume oil B | Equivalence % polyisocyanate in perfume oil B | % perfume leaking out of the capsule upon storage in softener at 43° C. for | |
|---|---|---|---|---|
| | | | 15 days | 30 days |
| I | 10% | 7.50% | 0 | 0.2 |
| J | 7.50% | 5.6% | 0.1 | 0.5 |
| K | 5% | 3.75% | 0.4 | 1.8 |
| L | 3% | 2.25% | 3 | 5.5 |
| M | 2% | 1.5% | 5 | 9 |
| N | 0.66% | 0.5% | 45 | 70 |

Leakage at 43° C. was found to be extremely low for all capsules I to M made according to the invention, in sharp contrast to the very high perfume leakage observed for capsule N outside the scope of this invention.

Figure 4:
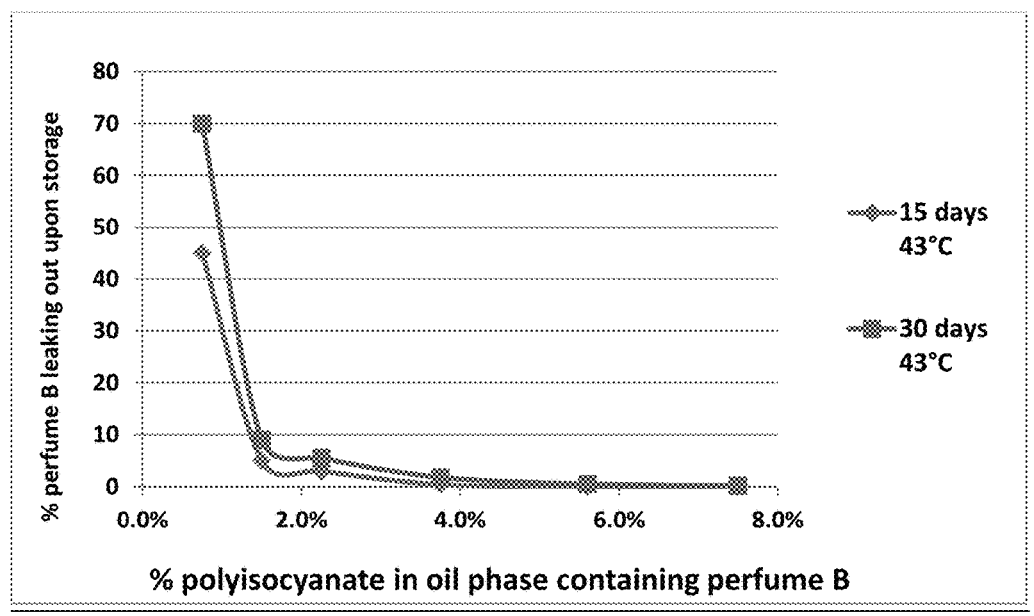
FIG. 4: represents the leakage of encapsulated perfume B upon storage in a fabric softener at 43° C. as a function of the percentage of polyisocyanate in the oil phase.

Results are represented on FIG. 4.

Again, the more polyisocyanate added in the oil, the better the stability (thicker wall). With already only 1.5% triisocyanate in the oil, the stability is very good, with less than 10% perfume leaking out of the capsule over 1 month storage at 43° C.

As for this perfume B best olfactive performance is achieved around 2 to 5% Takenate D-110N in the oil, for this perfume B, optimum between good encapsulation efficiency, stability & performance is around 2 to 5% Takenate® D-110N in the oil to be encapsulated. As Takenate D-110N is only 75% pure polyisocyanate, this is equivalent to 1.5% to 3.75% pure polyisocyanate needed in the perfume oil B to be encapsulated to achieve best combination of good storage stability and good olfactive impact for this perfume.

Example 6

Comparative Example Between Capsules According to the Invention and Capsules Wherein Polyamine (Guanidine) is Used as Co-Monomer Alongside with Takenate D-110N Capsules C were compared with capsules H (see Example 1). Capsules H are outside the scope of the invention are they are prepared with a process that includes adding polyamine (guanidine) as co-monomer.

TABLE 16

Encapsulation efficiency and storage stability of capsules C of the invention (no polyamine used) versus H (guanidine added in the process), once added in fabric-softener of example 3

| Capsule | % Takenate® D-110N in perfume oil A | Equivalence % polyisocyanate in perfume oil A | Use of polyamine (guanidine) | Encapsulation yield % | Storage stability in softener | | | |
|---|---|---|---|---|---|---|---|---|
| | | | | | 15 days | | 30 days | |
| | | | | | 35° C. | 43° C. | 35° C. | 43° C. |
| C | 5% | 3.75% | No | 99.3% | 3 | 12 | 4 | 18 |
| H | 5% | 3.75% | Yes | 99.3% | 1 | 9 | 3 | 15 |

Results show that performance is not lower in the absence of added polyamine in term of encapsulation efficiency and analytical stability (perfume leakage upon storage in softener). Analytically, perfume leakage out of capsule made with 5% Takenate® in the perfume oil is the same upon storage at 35° C. and only very slightly better if polyamines are used in the water phase for the most strenuous storage at 43° C.

Regarding olfactive impact comparison results are shown in Table 17.

TABLE 17 olfactive performance of capsules C of the invention (no polyamine used) versus H (guanidine added in the process), once added in fabric-softener of example 3

| | | | Perfume intensity | | | |
|---|---|---|---|---|---|---|
| | % Takenate D-110N in Perfume oil A | Use of polyamine (guanidine) | Using Fresh softener | | Using softener stored for 1 month at 35° C. | |
| Cap-sule | | | Before Rubbing | After Rubbing | Before Rubbing | After Rubbing |
| C | 5% | No | 3 | 6.4 | 2.55 | 5.8 |
| H | 5% | Yes | 2.8 | 6.1 | 2.5 | 5.85 |

Both capsules C & H show a strong & very similar rubbing effect.

Example 7

Preparation of Microcapsules Powders Containing Only Microcapsules as Source of Perfume An aqueous solution of 150 grams of water, 91 grams of the microcapsules of the invention and 100 grams of a mixture of starch and maltodextrin is prepared. The pH is set to pH 4 with pure citric acid added to the solution. The solution is then stirred vigorously using a Silverson L4RT high shear mixer.

The microcapsules dispersion was spray-dried on a SODEVA equipment (better to put Büchi Spray Dryer Model B 290). The temperature of the incoming air in the spray-dryer was 185° C.-190° C., the temperature of the outcoming air was 95° C.-105° C. a biphase spray nozzle was used with a nozzle diameter of 0.7 mm.

Example 8

Comparison of Storage Stability and Olfactive Performance Between Capsules According to the Invention and Aminoplast on the One Hand and Polyurea-Based Capsules on the Other Hand Synthesis Capsule V Aminoplast (not Part of the Invention)

The oil phase was prepared by admixing a polyisocyanate (trimethylol propane adduct of xylylene diisocyanate, Takenate® D-110N, origin: Mitsui Chemicals) with a perfume oil comprising the ingredients listed in Table 18. The oil phase consisted of 2% Takenate® D-110N and 98% of the perfume oil.

To make the capsules slurry, acrylamide and acrylic acid copolymers and a melamine-formaldehyde resin were dissolved in water to form the water phase. Then the perfume premix oil was added into this solution and the pH was regulated to 5 with acetic acid. The temperature was raised to 90° C. for 2 hours to allow the curing of the capsules. At this point, capsules were formed, cross-linked and stable. A 3% Salcare® SC60 (acrylamidepropyltrimonium chloride/acrylamide copolymer) solution in water was then added into the mixture at 90° C. and was allowed to react for 1 hour at 90° C. Then a solution of ethylene urea (50% wt in water) was added to scavenge residual free formaldehyde and the mixture was left to cool down to room temperature. The final pH was adjusted to 7 with sodium hydroxide.

TABLE 18

Composition of lead aminoplast Capsules V

| Ingredient | Capsule V [%] |
|---|---|
| Oil Phase | 30.9 |
| Perfume oil | 30.28 |
| Takenate ® D110N | 0.62 |
| Water phase | 69.1 |
| Acrylamide and acrylic acid copolymer[1] | 4.7 |
| Melamine-formaldehyde resins [2] | 2.45[3] |
| Water | 50.55 |
| Sodium hydroxyde | 0.5 |
| Acetic acid | 0.2 |
| Salcare ® SC60[3] | 10.7 |
| Total | 100 |

[1] Alcapsol ™ (Trademark from Ciba), 20% solution in water
[2] 90/10 blend of Cymel ® 385 (see above) & Cymel 9370 (highly methylated melamine) from Cytec, both 70% solution in water
[3] Salcare ® SC60 from Ciba (acrylamidopropyltrimonium chloride/acrylamide copolymer), 3% solution in water Anionic Polyurea capsule W to Z (not part of the invention) were made by reproducing Capsule G of WO2011/154893 which was the best balance of storage stability and olfactive performance on fabrics when used in fabric-softener of example 3.

TABLE 19

Composition of Anionic Polyurea Capsules W to Z (depending on perfume used)

| Ingredient | Amount [g] | Molar percentage, relative to total polyisocyanate |
|---|---|---|
| Desmodur ® N 100[1] | 9.4 | 35% |
| Takenate ® D-110N[2] | 33.2 | 65% |
| Perfume[3] | 400.0 | |
| Polyvinyl alcohol[4] | 5.5 | |
| Tetraethyl ammonium chloride[5] | 4.0 | |
| Guanidine carbonate[6] | 9.0 | |
| Water | 562.5 | |

[1] Biuret of hexamethylene diisocyanate (origin Bayer)
[2] Trimethylol propane-adduct of xylylene diisocyanate (origin: Mitsui Chemicals)
[3] Perfuming composition A for capsules W, B for capsules X, C for capsules Y or D for capsules Z of example 1 Table 3, 4, 5 or 6
[4] Mowiol ® 18-88, origin: Fluka
[5] Tetraethyl ammonium chloride (50% aqueous solution), origin: Fluka
[6] Origin: Acros Organics The Desmodur® N100 and the Takenate D-110N were dissolved in the perfume. This oil phase was introduced in a one litre glass double-jacketed reactor equipped with a scrapped stirrer and an Ika-rotor/stator system (6500-24000 rpm). The oil phase was stirred at 50 rpm with the scrapped stirrer for 5 minutes.

An aqueous stabilizer solution at 1% by weight, relative to the total weight of the stabilizer solution, was prepared by dissolving the polyvinyl alcohol in 543.5 g of deionised water. This solution was introduced into the reactor at room temperature and the scrapped stirrer was stopped.

A pre-emulsion was then prepared by dispersing the perfume phase in the aqueous phase with the Ika-rotor/stator system during 10 minutes at 13500 rpm.

Once the emulsion was prepared, the stirring was continued with the scrapped stirrer at 200 rpm until the end of the process.

The tetraethyl ammonium chloride solution was added to the emulsion. Then, a solution of the guanidine carbonate in 19 g of deionised water was added to the reactor over one hour. The temperature of the reaction mixture was then slowly increased over one hour from room temperature to 70° C. The temperature was then kept at 70° C. for two hours. The stirring speed was then decreased to 100 rpm and the capsules suspension was cooled down to room temperature.

The perfume content in the capsules suspension was around 40%, relative to the total weight of the suspension.

Cationic Polyurea capsule WW to ZZ (not part of the invention) were made by reproducing example 4 of WO2009/153695 which was the best balance of storage stability and olfactive performance on fabrics when used in fabric-softener and on Hair or Skin when used in BodyCare applications.

TABLE 20

Composition of Cationic Polyurea Capsules WW to ZZ

| Ingredient | Amount [g] |
|---|---|
| Desmodur® N 100[1] | 22.4 |
| Perfume[2] | 400.0 |
| Polyvinyl alcohol[3] | 1.4 |
| Luviquat Ultra Care[4] | 5.7 |
| Tetraethyl ammonium chloride[5] | 4.0 |
| Guanidine carbonate[6] | 5.3 |
| Water | 570.7 |

[1] Biuret of hexamethylene diisocyanate (origin Bayer)
[2] Perfuming composition A for capsules WW, B for capsules XX, C for capsules YY or D for capsules ZZ of example 1 Table 3, 4, 5 or 6
[3] Mowiol® 18-88, origin: Fluka
[4] Polyquaternium-44, BASF
[5] Tetraethyl ammonium chloride (50% aqueous solution), origin: Fluka
[6] Origin: Acros Organics The Desmodur® N100 was dissolved in the perfume. This oil phase was introduced in a one litre glass double-jacketed reactor equipped with a scrapped stirrer and an Ika-rotor/stator system (6500-24000 rpm). The oil phase was stirred at 50 rpm with the scrapped stirrer for 5 minutes.

An aqueous stabilizer solution at 0.25% by weight of polyvinyl alcohol and 1% of Luviquat Ultra Care, relative to the total weight of the stabilizer solution, was prepared by dissolving the polyvinyl alcohol and the luviquat in 570.7 g of deionised water. This solution was introduced into the reactor at room temperature and the scrapped stirrer was stopped.

A pre-emulsion was then prepared by dispersing the perfume phase in the aqueous phase with the Ika-rotor/stator system during 10 minutes at 13500 rpm.

Once the emulsion was prepared, the stirring was continued with the scrapped stirrer at 200 rpm until the end of the process.

The tetraethyl ammonium chloride solution was added to the emulsion. Then, a solution of the guanidine carbonate in 19 g of deionised water was added to the reactor over one hour. The temperature of the reaction mixture was then slowly increased over one hour from room temperature to 70° C. The temperature was then kept at 70° C. for two hours. The stirring speed was then decreased to 100 rpm and the capsules suspension was cooled down to room temperature.

The perfume content in the capsules suspension was around 40%, relative to the total weight of the suspension.

Storage Stability of Capsules in the Fabric Softener of Example 3

The storage stability of the capsules C (invention), V, W and WW (outside the invention) in the fabric-softener of example 3 was evaluated for up to one month at 43° C. The amount of perfume A having leaked out of the capsules overtime was measured by solvent extraction and GC-MS analysis. The results are summarized in the following Table 21.

TABLE 21

Stability of capsules C of the invention versus aminoplast capsules V, anionic polyurea capsule W and cationic polyurea capsule WW upon storage in fabric softener of example 3: Percentage of perfume A leaking overtime upon storage in softener at 43° C.

| | | % perfume leaking out of the capsule upon storage in softener at 43° C. for | |
|---|---|---|---|
| Capsule | Capsule type | 15 days | 30 days |
| C | Melamine-formaldehyde free | 12 | 18 |
| V | Aminoplast (Melamine-formaldehyde) | 14 | 22 |
| W | Anionic Polyurea | 22 | 28 |
| WW | Cationic Polyurea | 20 | 30 |

Storage stability in fabric-softener at 43° C. of capsule C of the invention is comparable and in fact even slightly better than stability of the capsules described in the art (melamine-formaldehyde capsule V, anionic polyurea W and cationic polyurea capsule WW)

The olfactive performance of Capsules C of the invention (with encapsulated perfume A) was also compared in fabric softener of example 3 to the performance of anionic polyurea capsule W and cationic polyurea WW, using the same protocol as described above for the olfactive performance of capsules A to G (with encapsulated perfume A). Slurry dosages were adjusted for each capsule C, W or WW so that all three softeners tested contain the same amount of encapsulated perfume A (0.05%).

The results are summarized in Table 22.

TABLE 22

Olfactive performance of capsules C of the invention in fabric-softener of example 3 compared to anionic polyurea capsule W and cationic polyurea capsule WW

| | | Encapsulated perfume oil A in softener | Perfume intensity | |
|---|---|---|---|---|
| Capsule | Capsule type | | Before Rubbing | After Rubbing |
| C | Melamine-formaldehyde free | 0.05% | 2.0 | 5.0 |
| W | Anionic Polyurea | 0.05% | 1.2 | 4.1 |
| WW | Cationic Polyurea | 0.05% | 1.2 | 4.3 |

At the same dosage of 0.05% encapsulated perfume A in fabric-softener, olfactive performance of capsule C of the invention is a clear improvement on lead anionic polyurea capsule W and lead cationic polyurea capsule WW

Example 9

Concentrated Liquid Detergent Containing Capsules

Liquid Detergents O to S were prepared by adding Capsules O to S at 0.3% by weight, relative to the total weight of the detergent into an un-perfumed concentrated liquid detergent base. This base (pH ~8) contains 5% to 15% of nonionic surfactants (such as alcohol ethoxylates) and anionic surfactants (such as sodium alkylbenzene sulphonate and sodium alkylether sulphate), with also less than 5% fatty soap.

Example 10

Olfactive Performance of the Capsules According to the Invention in Concentrated Liquid Detergent The olfactive performance of capsules O to S (all with encapsulated perfume C) was evaluated in Liquid Detergent of example 9.

Fabrics (2.5 kg of cotton terry towels) were washed at 40° C. in a standard European horizontal axis machine. There were dispensed 80 g of freshly prepared detergent at the start of the wash through the detergent drawer. After the wash, fabrics were line-dried and the odor intensity of the cotton towels was evaluated by a panel of 20 trained panelists, after 1 day drying. The panelists were asked to rate the odor intensity of the towels after gentle rubbing of the fabrics by hand on a scale from 1 to 7, 1 corresponding to odorless and 7 corresponding to a very strong odor. The results are shown in Table 23.

TABLE 23

Olfactive performance of Capsules O to S in concentrated liquid detergent as a function of % triisocyanate in Perfume oil C

| Capsule | % Takenate® D-110N in perfume oil C | Equivalence % polyisocyanate in perfume oil C | Perfume intensity Before Rubbing | Perfume intensity After Rubbing |
|---|---|---|---|---|
| O | 10% | 7.50% | 2.9 | 3.3 |
| P | 7.50% | 5.6% | 2.8 | 3.3 |
| Q | 5% | 3.75% | 2.7 | 3.4 |
| R | 3% | 2.25% | 2.7 | 3.4 |
| S | 2% | 1.5% | 2.6 | 2.6 |

Olfactively, all capsules O to S made according to the invention, e.g. using only a triisocyanate as sole monomer for the capsule walls at a concentration of at least 1.5% in the oil, do exhibit the required profile of some medium impact before rubbing, strongly amplified after rubbing (rubbing effect). Best olfactive performance is achieved when 3% to 10% polyisocyanate is added in the perfume oil.

Example 11

Storage Stability of the Capsules of the Invention in a Concentrated Liquid Detergent The storage stability of capsules O to S (made according to the invention) in Liquid Detergents of Example 9 were evaluated. The detergents comprising the capsules were stored to 4 weeks at 37° C. and the amount of perfume having leaked out of the capsules was measured by solvent extraction & GC-MS analysis. The results are summarized in the following table 24.

TABLE 24

Storage stability of the capsules of the invention in Liquid Detergents (LD) O to S.

| LD | % Takenate® D-110N in perfume oil C | Equivalence % polyisocyanate in perfume oil C | Amount of perfume that leaked out of the capsules [%] After 3 days at 37° C. | After 2 weeks at 37° C. | After 4 weeks at 37° C. |
|---|---|---|---|---|---|
| LD O | 10% | 7.50% | 1.0 | 2.4 | 3.7 |
| LD P | 7.50% | 5.6% | 2.1 | 5.3 | 8.3 |
| LD Q | 5% | 3.75% | 4.3 | 10.2 | 14.6 |
| LD R | 3% | 2.25% | 10.9 | 22.3 | 29.4 |
| LD S | 2% | 1.5% | 16.0 | 32.8 | 39.7 |

The more polyisocyanate in the oil, the better the stability (thicker wall). Capsules O to S made according to the invention show leakage below 40% after 4 weeks of storage at 37° C. For this perfume C, optimum between encapsulation efficiency, stability and performance is between 3 to 10% Takenate® D-110N in the oil to be encapsulated. As Takenate® D-110N is only 75% pure polyisocyanate, this is equivalent to 2.25% to 7.50% pure polyisocyanate needed in the perfume oil C to be encapsulated to achieve best combination of good storage stability and good olfactive impact for this perfume.

Example 12

Comparison of Storage Stability and Olfactive Performance Between Capsules According to the Invention and Polyurea-Based Capsules Storage Stability of Capsules in the Liquid Detergent of Example 9

The storage stability of the capsule Q (invention), Y and YY (outside the invention, described in example 8) in the liquid detergent of example 9 was evaluated for up to one month at 37° C. The amount of perfume C having leaked out of the capsules overtime was measured by solvent extraction and GC-MS analysis. The results are summarized in the following Table 25.

TABLE 25

Stability of capsules Q of the invention versus polyurea capsule Y and YY upon storage in liquid detergent of example 9: Percentage of perfume C leaking overtime upon storage in liquid detergent at 37° C.

| Capsule | Capsule type | % perfume leaking out of the capsule upon storage in liquid detergent at 37° C. for 15 days | 30 days |
|---|---|---|---|
| Q | Melamine-formaldehyde free | 9.5% | 14.6% |
| Y | Anionic Polyurea | 10.2% | 18.5% |
| YY | Cationic Polyurea | 10.0% | 16.4% |

Storage stability in liquid detergent at 37° C. of capsule Q of the invention is comparable and in fact even slightly better than the stability of the capsules described in the art (anionic polyurea capsule Y and cationic polyuera capsule YY)

The olfactive performance of Capsule Q of the invention (with encapsulated perfume C) was also compared in liquid detergent of example 9 to the performance of anionic polyurea capsule Y and the cationic polyurea capsule YY, using the same protocol as described above for the olfactive performance of capsules O to S (with encapsulated perfume C).

TABLE 26

Olfactive performance of capsule Q of the invention in liquid detergent of example 9 compared to anionic polyurea capsule Y and cationic polyurea capsule YY

| Capsule | Capsule type | Encapsulated perfume oil C in liquid detergent | Perfume intensity Before Rubbing | Perfume intensity After Rubbing |
|---|---|---|---|---|
| Q | Melamine-formaldehyde free | 0.1% | 2.7 | 3.4 |
| Y | Anionic Polyurea | 0.1% | 1.5 | 2.0 |
| YY | Cationic Polyurea | 0.1% | 2.5 | 2.9 |

At the same dosage of 0.1% encapsulated perfume C in liquid detergent, olfactive performance of capsule Q of the invention is a clear improvement on lead anionic polyurea capsule Y and cationic polyurea capsule YY.

Example 13

Roll-on Antiperspirant Deodorant Product Comprising the Capsules of the Invention

TABLE 27

Composition of the anti-perspirant roll-on emulsion formulation

| Ingredient | Amount [%] w/w |
|---|---|
| Steareth-2 | 3.25% |
| Steareth-21 | 0.75% |
| PPG-15 Stearyl Ether | 4% |
| Aluminium Chlorohydrate | 20% |
| Water | 41% |

Roll-ons I to N were prepared by adding Capsules I and K to N at 1% by weight, relative to the total weight of the roll-on into the un-perfumed roll-on base of Table 27.

Example 14

Olfactive Performance of the Capsules According to the Invention in Anti-Perspirant Roll on The olfactive performance of Capsules I and K to M of the invention and N (outside of the invention) was evaluated in the anti-perspirant roll-on emulsion formulation of example 13. 0.15 g of product was spread on a paper blotter (4.5 cm*12 cm) and left to dry for 1 h at room temperature before evaluating.

The intensity of the perception of the perfume on the blotters treated with the above roll-on formulation was evaluated by a panel of 10 trained panellists. They were asked to rub gently the blotters with one finger and then to rate the intensity of the perfume perception on a scale ranging from 1 to 7, wherein 1 means no odour and 7 means very strong odour. The results are summarized in the following table 28.

TABLE 28

Olfactive performance of capsules I and K to M of the invention and N (outside the invention) in roll-on of Example 13, as a function of % triisocyanate in Perfume oil B

| Capsule | % Takenate ® D-110N perfume oil B | Equivalence % poly-isocyanate in perfume oil B | Perfume intensity fresh Before Rubbing | Perfume intensity fresh After Rubbing | Perfume intensity 12 weeks/45° C. Before Rubbing | Perfume intensity 12 weeks/45° C. After Rubbing |
|---|---|---|---|---|---|---|
| I | 10% | 7.50% | 3.7 | 5.5 | 2.5 | 5.8 |
| K | 5% | 3.75% | 4.1 | 6.3 | 3.7 | 6.5 |
| L | 3% | 2.25% | 4.5 | 6.2 | 4.2 | 6.5 |
| M | 2% | 1.5% | 4.7 | 6.0 | 4.2 | 6.2 |
| N | 0.66% | 0.5% | 4.7 | 5.0 | 3.7 | 5.2 |

Olfactively, all capsules I to M made according to the invention, e.g. using only a triisocyanate as sole monomer for the capsule walls at a concentration of at least 1% in the oil, do exhibit the required profile of some medium impact before rubbing, strongly amplified after rubbing (rubbing effect). Best olfactive performance is achieved when 2% to 5% polyisocyanate is added in the perfume oil.

Capsule N using very low concentration of isocyanate outside the scope of the invention is olfactively weaker than all capsules I to M of the invention, showing in particular poorer impact after rubbing.

Example 15

TABLE 29

Storage stability of capsules I to M of the invention and N (outside the invention) upon storage in roll-on of example 13: % perfume leaking overtime upon storage in roll-on at 45° C.

| Capsule | % Takenate ® D-110N in perfume oil B | Equivalence % polyisocyanate in perfume oil B | % perfume leaking out of the capsule upon storage in roll-on at 45° C. for 4 weeks | % perfume leaking out of the capsule upon storage in roll-on at 45° C. for 12 weeks |
|---|---|---|---|---|
| I | 10% | 7.50% | 0.9% | 3.6% |
| K | 5% | 3.75% | 8.4% | 14.5% |
| L | 3% | 2.25% | 10.0% | 13.1% |
| M | 2% | 1.5% | 12.0% | 15.5% |
| N | 0.66% | 0.5% | 35.1% | 47.0% |

Leakage at 45° C. was found to be extremely low for all capsules I to M made according to the invention, in sharp contrast to the very high perfume leakage observed for capsule N outside the scope of this invention.

Example 16

Comparison of Storage Stability and Olfactive Performance Between Capsules According to the Invention and Polyurea-Based Capsules The storage stability of the capsule K (invention), X and XX (outside the invention, described in example 8) in the roll-on of example 13 was evaluated for up to one month at 37° C. The amount of perfume B having leaked out of the capsules overtime was measured by solvent extraction and GC-MS analysis. The results are summarized in the following Table 30.

TABLE 30

Stability of capsules K of the invention versus polyurea capsule.
X and XX upon storage in roll-on of example 13: Percentage of perfume
B leaking overtime upon storage in roll-on at 45° C.

| | | % perfume leaking out of the capsule upon storage in roll-on at 45° C. for | |
|---|---|---|---|
| Capsule | Capsule type | 4 weeks | 12 weeks |
| K | Melamine-formaldehyde free | 8% | 14.5% |
| X | Anionic Polyurea | 8.4% | 15% |
| XX | Cationic Polyurea | 8% | 14.9% |

Storage stability in roll-on at 45° C. of capsule K of the invention is comparable to the stability of the capsules X and XX described in the art (polyurea capsules)

The olfactive performance of Capsule K of the invention (with encapsulated perfume B) was also compared in roll-on of example 13 to the performance of anionic polyurea capsule X and cationic polyurea capsule XX, using the same protocol as described above for the olfactive performance of capsules I to N (with encapsulated perfume B).

TABLE 31

Olfactive performance of capsule K of the invention
in roll-on of example 13 compared to anionic polyurea
capsule X and cationic polyurea capsule XX

| | | Encapsulated perfume | Perfume intensity fresh | |
|---|---|---|---|---|
| Capsule | Capsule type | oil B in roll-on | Before Rubbing | After Rubbing |
| K | Melamine-formaldehyde free | 0.4% | 4.1 | 6.3 |
| X | Anionic Polyurea | 0.4% | 2.5 | 5.0 |
| XX | Cationic Polyurea | 0.4% | 2.5 | 5.0 |

At the same dosage of 0.4% encapsulated perfume K in roll-on, olfactive performance of capsule K of the invention is a clear improvement on lead anionic polyurea capsule X and lead cationic polyurea capsule XX.

Example 17

Body Wash Product Comprising the Capsules of the Invention and Olfactive Evaluation Thereof A body wash formulation was prepared having the following ingredients in the amount indicated.

TABLE 32

Composition of the body wash formulation

| Ingredient | Amount [%] w/w |
|---|---|
| Carbopol ® Aqua CC polymer[1] | 8.0 |
| Citric acid (40% solution in water) | 0.5 |
| Zetesol AO 328 U[2] | 25.0 |
| Tego Betain F 50[3] | 4.0 |
| Glydant Plus Liquid[4] | 0.1 |
| Sodium Chloride (20% solution in water) | 4.0 |
| Water | 58.4 |

[1]Polyacrylate-1 crosspolymer, origin and trademark: Noveon
[2]Sodium $C_{12}$-$C_{15}$ pareth sulfate, origin and trademark: Zschimmer & Schwarz
[3]Cocamidopropyl betaine, origin and trademark: Goldschmidt AG
[4]DMDM hydantoin and iodoproynyl butylcarbamate, origin and trademark: Lonza

Example 18

Storage Stability of Capsules in the Body Wash of Example 17

The storage stability of the capsules T and U (of the invention), and Z and ZZ (outside the invention, described in example 8) in the body wash of example 17 was evaluated for up to one month at 45° C. and 1 week at 50° C. The amount of perfume D having leaked out of the capsules overtime was measured by solvent extraction and GC-MS analysis. The results are summarized in the following Table 33.

TABLE 33

Stability of capsules T and U of the invention versus polyurea capsules
Z and ZZ upon storage in body wash of example 17: Percentage of perfume
D leaking overtime upon storage in Body Wash at 45° C. and 50° C.

| | | % perfume leaking out of the capsule upon storage in body wash at 45° C. for | | % perfume leaking out of the capsule upon storage in body wash at 50° C. for |
|---|---|---|---|---|
| Capsule | Capsule type | 15 days | 30 days | 1 week |
| T | Melamine-formaldehyde free | 0 | 0 | 0 |
| U | Melamine-formaldehyde free | 0 | 0 | 0 |
| Z | Anionic Polyurea | 0 | 0 | 0 |
| ZZ | Cationic Polyurea | 0 | 0 | 0 |

Storage stability in body wash at 40° C. and 50° C. of capsules T and U of the invention is comparable to the stability of the capsules described in the anionic polyurea capsule Z and cationic polyurea capsule ZZ, with no detectable perfume leakage from these various capsules upon storage.

Capsules were respectively dispersed in the body wash formulation prepared above in example 17.

Body Washes were applied to the forearms, 1 g of the Body Washes from example 17 was then respectively applied with a micropipette and lather was then created during 10 seconds on the forearm. The arms were then rinsed during 10 s under running water at 38° C. and finally allowed to dry with a towel.

The perfume intensity was then evaluated on a blind basis by an expert panel consisting of 4 trained panelists who were asked to rate the perceived perfume intensity on the arms after rubbing the arm with a finger, on a scale ranging from 1 to 7, wherein 1 means no odor and 7 means very strong odor. Evaluation was done straight after application (fresh) and also a few hours (4 h and 6 h after application).

TABLE 34

Olfactive performance of capsules T and U of the invention in body wash of example 17 compared to anionic polyurea capsule Z and cationic polyurea capsule ZZ

| Capsule | Capsule type | Encapsulated perfume oil D in Body Wash | Perfume intensity | | | | | |
|---|---|---|---|---|---|---|---|---|
| | | | Before Rubbing fresh | After Rubbing fresh | Before Rubbing 4 h | After Rubbing 4 h | Before Rubbing 6 h | After Rubbing 6 h |
| T | Melamine formaldehyde free | 0.25% | 3.5 | 6.4 | 1.8 | 3.7 | 1.0 | 2.0 |
| U | Melamine formaldehyde free | 0.25% | 3.5 | 6.3 | 2.2 | 4.1 | 1.5 | 2.4 |
| Z | Anionic Polyurea | 0.25% | 1.0 | 2.5 | 1.0 | 1.0 | 1.0 | 1.0 |
| ZZ | Cationic Polyurea | 0.25% | 1.4 | 2.6 | 1.0 | 2.0 | 1.0 | 1.25 |

At the same dosage of 0.25% encapsulated perfume D in body wash, olfactive performance of capsules T and U of the invention is a clear improvement on lead anionic polyurea capsule Z and cationic polyurea capsule ZZ.

Example 19

Hair Shampoo Product Comprising the Capsules of the Invention and Olfactive Evaluation Thereof

TABLE 35

Composition of the shampoo formulation

| Ingredient | Amount [%] w/w |
|---|---|
| Jaguar C-14S [1] (Rodhia) | 0.4% |
| Dehyton AB-30 [2] (Cognis) | 7% |
| Texapon NSO IS [3] (Cognis) | 45.0% |
| Dow Corning 2-1691 emulsion [4] | 3% |
| Cutina AGS [5] (Cognis) | 0.9% |
| Rewomid IPP 240 [6] (Degussa) | 1.2% |
| Cetyl alcohol | 1.2% |
| Glydant plus liquid [7] (Lonza) | 0.3% |
| Water | 41% |

[1] Guar Hydroxypropyltrimonium chloride, origin and trademark from Rhodia, France
[2] Coco-Betaine, orign and trademark from Cognis, Germany
[3] Sodium Laureth Sulfate, orign and trademark from Cognis, Germany
[4] Dimethicone and Lureth-23 and Laureth-4 and Salicylic Acid, orign and trademark from Dow Corning, UK
[5] Glycol Distearate, orign and trademark from Cognis, Germany
[6] CocoAmide MPA, orign and trademark from Degussa, Germany
[7] DMDM Hydantoin and Iodopropynyl ButylCarbamate, orign and trademark from Lonza, UK The olfactive performance of Capsules T and U of the invention and Z and ZZ (outside the invention, described in example 8) was evaluated in the above hair shampoo formulation in table 35. Capsules were respectively dispersed in the shampoo formulation prepared above. A 10 g hair swatch was first washed with 2.5 g of this shampoo formulation containing capsules, rinsed for 30 seconds under tap water at 37° C. before repeating the same wash/rinse operation a second time. The hair swatch was then left to dry for 6 h at room temperature before evaluating.

Example 20

Storage Stability of Capsules in the Hair Shampoo of Example 19

The storage stability of the capsules T and U (invention) and Z and ZZ (outside the invention, described in example 8) in the Hair Shampoo of example 19 was evaluated for up to one month at 45° C. The amount of perfume D having leaked out of the capsules overtime was measured by solvent extraction and GC-MS analysis. The results are summarized in the following Table 36.

TABLE 36

Stability of capsules T and U of the invention versus polyurea capsule Z and ZZ upon storage in Hair Shampoo of example 19: Percentage of perfume D leaking overtime upon storage in Hair Shampoo at 45° C.

| | | % perfume leaking out of the capsule upon storage in Hair Shampoo at 45° C. for | |
|---|---|---|---|
| Capsule | Capsule type | 15 days | 30 days |
| T | Melamine-formaldehyde free | 0 | 0 |
| U | Melamine-formaldehyde free | 0 | 0 |
| Z | Anionic Polyurea | 0 | 0 |
| ZZ | Cationic Polyurea | 0 | 0 |

Storage stability in body wash at 45° C. of capsules T and U of the invention is comparable to the stability of the capsules described in the anionic polyurea capsule Z and cationic polyurea capsule ZZ, with no detectable perfume leakage from these various capsules upon storage.

The intensity of the perception of the perfume on the hair swatches washed with the above Hair Shampoo formulation was evaluated by a panel of 10 trained panellists. They were asked to comb gently the hair swatches 3 times and then to rate the intensity of the perfume perception on a scale ranging from 1 to 7, wherein 1 means no odour and 7 means very strong odour.

TABLE 37

Olfactive performance of capsules T and U of the invention versus polyurea capsule Z and Z in Hair Shampoo of example 19

| Capsule | Capsule type | Encapsulated perfume oil D in Hair Shampoo | Perfume intensity fresh | | Perfume intensity after 1 month 45° C. | |
|---|---|---|---|---|---|---|
| | | | Before combing | After combing | Before combing | After combing |
| T | Melamine formaldehyde free | 0.2% | 2.5 | 4.0 | 2.5 | 5.0 |
| U | Melamine formaldehyde free | 0.2% | 3.0 | 5.0 | 3.3 | 6.1 |
| Z | Anionic Polyurea | 0.2% | 2 | 2 | 1.9 | 2.1 |
| ZZ | Cationic Polyurea | 0.2% | 2 | 2.5 | 1.4 | 3.1 |

At the same dosage of 0.2% encapsulated perfume D in Hair Shampoo, olfactive performance of capsules T and U of the invention is a clear improvement on lead anionic polyurea capsule Z and cationic polyurea capsule ZZ.

Example 21

Rinse-Off Hair Conditioner Product Comprising the Capsules of the Invention and Olfactive Evaluation Thereof

TABLE 38

Composition of the internal ROC base

| Ingredient | Amount [%] w/w |
|---|---|
| Natrosol 250 H [1] (Hercules) | 1.0% |
| Dehyquart C 4046 [2] (Cognis) | 0.2% |
| Mirasil ADM-E [3] (Rhodia) | 1.2% |
| Genamin KDM [4] (Clariant) | 1.0% |
| Crodamol SS [5] (Croda) | 0.5% |
| Crodacol C 90 [6] (Croda) | 3.0% |
| Nipagin M [7] (NIPA) | 0.3% |
| Water | 92.25% |

[1] Hydroxyethylcellulose, origin and trademark from Hercules, Germany
[2] Cetearyl alcohol and Dipalmitoylethyl Hydroxyethylmonium methosulfate and ceteareth-20, origin and trademark from Cognis, Switzerland
[3] Amodimethicone and trideceth-6, origin and trademark from Rhodia, France
[4] Behentrimonium chloride, origin and trademark from Clariant, Germany
[5] Cetyl esters, origin and trademark from Croda, UK
[6] Cetyl Alcohol, origin and trademark from Croda, UK
[7] Methyl paraben, origin and trademark from NIPA, Switzerland The olfactive performance of Capsules T, U (of the invention) and Z and ZZ (outside of the invention, described in example 8) was evaluated in the above rinse-off hair-conditioner formulation. Capsules were respectively dispersed in the above rinse-off hair-conditioner product. A 10 g hair swatch is first washed with 2.5 g of the shampoo formulation of example 19 (unperfumed and without capsules), rinsed for 30 seconds under tap water at 37° C. before spreading 0.5 g of above rinse-off hair-conditioner formulation with capsules. The hair swatches are then rinsed for 30 seconds under tap water at 37° C. and left to dry for 6 h at room temperature before evaluating.

Example 22

Storage Stability of Capsules in the Rinse-Off Hair Conditioner of Example 21

The storage stability of the capsules T and U (invention), Z and ZZ (outside the invention, described in example 8) in the Rinse-off hair conditioner of example 21 was evaluated for up to one month at 45° C. The amount of perfume D having leaked out of the capsules overtime was measured by solvent extraction and GC-MS analysis. The results are summarized in the following Table 39.

TABLE 39

Stability of capsules T and U of the invention versus polyurea capsule Z and ZZ upon storage in Rinse-off hair conditioner of example: Percentage of perfume D leaking overtime upon storage in Rinse-off hair conditioner at 45° C.

| | | % perfume leaking out of the capsule upon storage in Rinse-off hair conditioner at 45° C. for | |
|---|---|---|---|
| Capsule | Capsule type | 15 days | 30 days |
| T | Melamine-formaldehyde free | 0 | 0 |
| U | Melamine-formaldehyde free | 0 | 0 |
| Z | Anionic Polyurea | 0 | 0 |
| ZZ | Cationic Polyurea | 0 | 0 |

Storage stability in Rinse-off hair conditioner at 40° C. of capsules T and U of the invention is comparable to the stability of the capsules described in the anionic polyurea capsule Z and cationic polyurea capsule ZZ, with no detectable perfume leakage from these various capsules upon storage.

The intensity of the perception of the perfume on the hair swatches washed with the above Rinse-off hair conditioner formulation was evaluated by a panel of 10 trained panellists. They were asked to comb gently the hair swatches 3 times and then to rate the intensity of the perfume perception on a scale ranging from 1 to 7, wherein 1 means no odour and 7 means very strong odour.

TABLE 40

Olfactive performance of capsules T and U of the invention versus polyurea capsule Z and ZZ in Rinse-off conditioner of example 21

| Capsule | Capsule type | Encapsulated perfume oil D in Rinse-off hair conditioner | Perfume intensity Before combing | After combing |
|---|---|---|---|---|
| T | Melamine formaldehyde free | 0.2% | 2.5 | 4.5 |
| U | Melamine formaldehyde free | 0.2% | 3.0 | 5.5 |
| Z | Anionic Polyurea | 0.2% | 2 | 2 |
| ZZ | Cationic Polyurea | 0.2% | 2 | 2.5 |

At the same dosage of 0.2% encapsulated perfume D in Rinse-off hair conditioner, olfactive performance of capsules T and U of the invention is a clear improvement on lead anionic polyurea capsule Z and cationic polyurea capsule ZZ.

Example 23

Leave-on Hair Conditioner Product Comprising the Capsules of the Invention and Olfactive Evaluation Thereof

TABLE 41

Composition of the leave-on hair conditioner formulation

| Ingredient | Amount [%] w/w |
|---|---|
| Water | 95.5% |
| Mirasil ADM-E [1] (Rhodia) | 1.5% |
| Salcare SC 91 [2] (Ciba) | 1.0% |
| Aculyn 46 [3] (Rohm & Haas) | 1.0% |
| Wacker-Belsil DMC 6038 [4] | 0.5% |
| Phenonip [5] (Clariant) | 0.5% |

[1] Amodimethicone and trideceth-6, origin and trademark from Rhodia, France
[2] Sodium Acrylates Copolymer and Mineral oil and PPG-1 trideceth-6, orign and trademark from Ciba (BASF now), Germany
[3] PEG-150/Stearyl Alcohol/SMDI Copolymer, orign and trademark from Rohm & Haas, Germany
[4] Dimethicone Copolyol, orign and trademark from Wackherr, Germany
[5] Butylparaben and ethylparaben and methylparaben and propylparaben and phenoxyethanol, orign and trademark from Clariant, Germany The olfactive performance of Capsules T and U (of the invention), Z and ZZ (outside the invention) was evaluated in the leave-on hair conditioner formulation above in table 41. Capsules were respectively dispersed in this leave-on hair conditioner formulation. A 10 g hair swatch is first washed with 2.5 g of the shampoo formulation of example 19 (unperfumed and without capsules), rinsed for 30 seconds under tap water at 37° C. before spreading 0.5 g of above leave-on hair-conditioner formulation with capsules. The hair swatches are left to dry for 6 h at room temperature before evaluating.

Example 24

Storage Stability of Capsules in the Leave-on Hair Conditioner of Example 23

The storage stability of the capsules T and U (of the invention), Z and ZZ (outside the invention, described in example 8) in the Leave-on hair conditioner of example 23 was evaluated for up to one month at 45° C. The amount of perfume D having leaked out of the capsules overtime was measured by solvent extraction and GC-MS analysis. The results are summarized in the following Table 42.

TABLE 42

Stability of capsules T and U of the invention versus polyurea capsule Z and ZZ upon storage in Leave-on hair conditioner of example 23: Percentage of perfume D leaking overtime upon storage in Leave-on hair conditioner at 45° C.

| | | % perfume leaking out of the capsule upon storage in Leave-on hair conditioner at 45° C. for | |
|---|---|---|---|
| Capsule | Capsule type | 15 days | 30 days |
| T | Melamine-formaldehyde free | 0 | 0 |
| U | Melamine-formaldehyde free | 0 | 0 |
| Z | Anionic Polyurea | 0 | 0 |
| ZZ | Cationic Polyurea | 0 | 0 |

Storage stability in Leave-on hair conditioner at 45° C. of capsules T and U of the invention is comparable to the stability of the capsules described in the anionic polyurea capsule Z and cationic polyurea capsule ZZ, with no detectable perfume leakage from these various capsules upon storage.

The intensity of the perception of the perfume on the hair swatches washed with the above Leave-on hair conditioner formulation was evaluated by a panel of 10 trained panellists. They were asked to comb gently the hair swatches 3 times and then to rate the intensity of the perfume perception on a scale ranging from 1 to 7, wherein 1 means no odour and 7 means very strong odour.

TABLE 43

Olfactive performance of capsules T and U of the invention versus polyurea capsule Z and ZZ in Leave-on conditioner of example 23

| Capsule | Capsule type | Encapsulated perfume oil D in Leave-on hair conditioner | Perfume intensity Before combing | After combing |
|---|---|---|---|---|
| T | Melamine formaldehyde free | 0.2% | 4.5 | 7 |
| U | Melamine formaldehyde free | 0.2% | 4.7 | 7 |
| Z | Anionic Polyurea | 0.2% | 3 | 7 |
| ZZ | Cationic Polyurea | 0.2% | 3 | 7 |

At the same dosage of 0.2% encapsulated perfume D in Leave-on hair conditioner, olfactive performance of capsules T and U of the invention is better before rubbing and comparable after combing to the lead anionic polyurea capsule Z and cationic polyurea capsule ZZ.

What is claimed is:

1. A process for the preparation of a melamine-formaldehyde free microcapsule comprising the steps of:
   1) admixing a perfume or flavour oil with at least one polyisocyanate having at least three isocyanate functional groups to form an oil phase, provided that the oil phase is essentially free from diisocyanate;
   2) dissolving an ionic surfactant or ionic colloidal stabilizer in water to form a water phase;
   3) adding the oil phase to the water phase to form an oil-in-water dispersion, wherein the mean droplet size is comprised between 1 and 500 μm;
   4) performing a curing step to polymerize the polyisocyanate(s) in the dispersion, wherein the polyisocyanate(s) is the sole monomer, to form a slurry of microcapsules that are essentially free from melamine formaldehyde;
   wherein the at least one polyisocyanate has at least three isocyanate functional groups and is present in an amount comprised between 1 and 15 wt % of the oil phase, the water phase is essentially free from melamine-formaldehyde and no amine or polyamine is added at any stage of the process.

2. A process according to claim 1, further comprising the step of adding a polymer selected from the group consisting of a non-ionic polysaccharide, a cationic polymer and mixtures thereof to form an outer coating to the microcapsule.

3. The process according to claim 1, further comprising the step of drying the capsule slurry to obtain dried microcapsules.

4. The process according to claim 1, characterized in that the at least one polyisocyanate having at least three isocyanate functional groups is present in an amount comprised between 2 and 8 wt % of the oil phase and the water phase includes an acrylamide/acrylic acid copolymer.

5. The process according to claim 1, characterised in that the at least one polyisocyanate having at least three isocyanate functional groups is present in an amount comprised between 2 and 6 wt % of the oil phase and the water phase includes an acrylamide/acrylic acid copolymer.

6. The process according to claim 1, characterized in that the at least one polyisocyanate having at least three isocyanate functional groups is a mixture of at least one aliphatic polyisocyanate and at least one aromatic polyisocyanate, the aliphatic polyisocyanate and the aromatic polyisocyanate being in a respective molar ratio ranging from 80:20 to 10:90.

7. The process according to claim 1, characterized in that the at least one polyisocyanate having at least three isocyanate functional groups is an aromatic polyisocyanate.

8. The process according to claim 1, characterised in that oil phase consists essentially of the perfume or flavour oil with the at least one polyisocyanate having at least three isocyanate functional groups.

9. The process according to claim 1, characterised in that the curing step is performed at a temperature comprised between 50 and 130° C., for 15 min to 8 hours.

10. A melamine-formaldehyde free microcapsule obtained by a process as defined in claim 1.

11. A microcapsule according to claim 10, having a core-shell morphology and
a core comprising a perfume or flavour oil;
a shell consisting essentially of polymerised polyisocyanate formed from at least one polyisocyanate comprising at least three isocyanate functional groups.

12. A perfuming composition comprising;
(i) microcapsules as defined in claim 10;
(ii) at least one ingredient selected from the group consisting of a perfumery carrier and a perfumery co-ingredient; and
(iii) optionally at least one perfumery adjuvant.

13. A liquid perfumed consumer product comprising:
a) from 2 to 65% by weight, relative to the total weight of the consumer product, of at least one surfactant;
b) water or a water-miscible hydrophilic organic solvent; and
c) microcapsules as defined in claim 11.

14. A liquid perfumed consumer product according to claim 13, characterised in that the product is a home- or personal-care product.

15. A powder perfumed product comprising
(a) from 2 to 65% by weight, relative to the total weight of the consumer product, of at least one surfactant; and
(b) microcapsules obtained by a process according to claim 1.

16. The process of claim 1, wherein the mean droplet size is between 5 and 50 microns.

17. The process of claim 9, wherein the curing step is performed at a temperature between 50 and 95° C. for between 30 min and 4 hours.

18. The process of claim 9, wherein the curing step is performed at a temperature between 75 and 90° C. for between 1 hour and 4 hours.

19. A perfuming composition comprising;
(i) microcapsules as defined in claim 11;
(ii) at least one ingredient selected from the group consisting of a perfumery carrier and a perfumery co-ingredient; and
(iii) optionally at least one perfumery adjuvant.

20. A powder perfumed product comprising
(a) from 2 to 65% by weight, relative to the total weight of the consumer product, of at least one surfactant; and
(b) microcapsules obtained by a process according to claim 4.

* * * * *